(12) United States Patent
Shi et al.

(10) Patent No.: US 11,231,431 B2
(45) Date of Patent: Jan. 25, 2022

(54) ULTRASOUND IMAGING DEVICE AND IMAGING METHOD THEREOF

(71) Applicant: SHENZHEN MINDRAY BIO-MEDICAL ELECTRONICS CO., LTD., Shenzhen (CN)

(72) Inventors: Zhiwei Shi, Shenzhen (CN); Ziyan Zhu, Shenzhen (CN); Lei Zhu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 493 days.

(21) Appl. No.: 15/198,457

(22) Filed: Jun. 30, 2016

(65) Prior Publication Data

US 2016/0302759 A1 Oct. 20, 2016

Related U.S. Application Data

(63) Continuation of application No. PCT/CN2014/077330, filed on May 13, 2014.

(30) Foreign Application Priority Data

Dec. 30, 2013 (CN) .......................... 201310746549.0

(51) Int. Cl.
*A61B 8/08* (2006.01)
*A61B 8/13* (2006.01)
(Continued)

(52) U.S. Cl.
CPC .......... *G01N 35/021* (2013.01); *A61B 8/0825* (2013.01); *A61B 8/13* (2013.01);
(Continued)

(58) Field of Classification Search
CPC ....... A61B 8/4461; A61B 8/0825; A61B 8/13; A61B 8/14; A61B 8/00; A61B 8/54;
(Continued)

(56) References Cited

U.S. PATENT DOCUMENTS

| 4,137,777 A | * | 2/1979 | Haverl | ...................... A61B 8/08 73/620 |
| 4,917,096 A | * | 4/1990 | Englehart | ............ A61B 8/0825 600/446 |

(Continued)

FOREIGN PATENT DOCUMENTS

| CN | 1469723 A | 1/2004 |
| EP | 2468190 A1 | 6/2012 |

(Continued)

OTHER PUBLICATIONS

Ihnatsenka et al.; U;trasound: Basic understanding and learning the language; 2010; International Journal of Shoulder Surgery; 4(3): 55-62.*

*Primary Examiner* — Christopher Koharski
*Assistant Examiner* — Kaitlyn E Selmer
(74) *Attorney, Agent, or Firm* — Kory D. Christensen

(57) ABSTRACT

A 3D ultrasound imaging device including an ultrasound probe assembly and echo analyzer. The ultrasound probe assembly includes a housing and an acoustic window abutted against the housing to form a sealed chamber, wherein the surface of the acoustic window contacts with the breast of the human body to be examined; an ultrasound transducer moves at a first speed back and forth within the sealed chamber and performs high-speed pre-scanning through the acoustic window to obtain initial ultrasound signals; the echo analyzer analyzes the initial ultrasound signals to determine a quality of a ultrasound image acquired by the high speed pre-scanning; and the ultrasound transducer then
(Continued)

moves at a second speed to perform another scan to acquire new ultrasound signals. A 3D ultrasound imaging method is also disclosed.

34 Claims, 19 Drawing Sheets

(51) Int. Cl.
*A61B 8/00* (2006.01)
*A61B 8/14* (2006.01)
*G01N 35/02* (2006.01)
*G01N 35/00* (2006.01)
*G01N 35/04* (2006.01)

(52) U.S. Cl.
CPC .............. *A61B 8/14* (2013.01); *A61B 8/4245* (2013.01); *A61B 8/4461* (2013.01); *A61B 8/52* (2013.01); *A61B 8/523* (2013.01); *A61B 8/5215* (2013.01); *A61B 8/5269* (2013.01); *A61B 8/54* (2013.01); *G01N 35/00594* (2013.01); *A61B 8/4427* (2013.01); *A61B 8/5292* (2013.01); *G01N 2035/0413* (2013.01)

(58) Field of Classification Search
CPC ......... A61B 8/5215; A61B 8/523; A61B 8/52; A61B 8/5269; A61B 8/4245; A61B 8/5292; A61B 8/4427; G01N 35/021; G01N 35/00594; G01N 2035/0413
See application file for complete search history.

(56) References Cited

U.S. PATENT DOCUMENTS

| | | | | |
|---|---|---|---|---|
| 5,181,513 A | * | 1/1993 | Touboul | A61B 5/02007 600/443 |
| 6,574,499 B1 | | 6/2003 | Dines et al. | |
| 2006/0241461 A1 | * | 10/2006 | White | A61B 8/06 600/454 |
| 2007/0010742 A1 | * | 1/2007 | Torp | A61B 5/6843 600/437 |
| 2008/0025145 A1 | * | 1/2008 | Peszynski | A61B 8/12 367/7 |
| 2010/0069756 A1 | * | 3/2010 | Ogasawara | A61B 8/08 600/447 |
| 2011/0301461 A1 | | 12/2011 | Anite | |
| 2012/0083692 A1 | * | 4/2012 | Stoll | A61B 8/0858 600/437 |
| 2012/0157831 A1 | * | 6/2012 | Waki | A61B 8/4461 600/427 |
| 2013/0237826 A1 | * | 9/2013 | Levien | A61B 8/4461 600/448 |
| 2014/0169672 A1 | * | 6/2014 | Zhu | G06K 9/4642 382/170 |

FOREIGN PATENT DOCUMENTS

| | | |
|---|---|---|
| JP | 2008200096 A | 9/2008 |
| WO | 2013171671 A1 | 11/2013 |

* cited by examiner

ULTRASOUND IMAGING DEVICE AND IMAGING METHOD THEREOF

TECHNICAL FIELD

The present disclosure relates to the medical technology field and particularly to an ultrasound imaging device and method thereof.

BACKGROUND

Ultrasound is one of the most important imaging tools in breast screening. The ultrasound examination has no radiation, it is convenient to use, and the cost is low. The ultrasound examination is beneficial and does not cause damage to people with large glands or dense glands and young women, especially near the pectorals.

The technology of automatic breast scanning has developed in recent years. It scans the breast tissue using a mechanical scanning device and then constructs models, thereby allowing doctors to observe the breast tissue in coronal planes and obtain results normal ultrasound imaging cannot achieve.

The technical idea of full breast scanning includes a water immersion method and direct contact method. The water immersion method further includes supine type and prone type. With the water immersion method, a patient's breast is immersed in water directly or separated by an ultrasound transparent layer when the patient is at a supine position, or the patient's breast is covered by a water bag when the patient is at a prone position and a ultrasound probe in the water rotates around and scans the breast. An advantage of the supine position is that the breast has no deformation during the scanning process, and a disadvantage is that the peripheral mammary gland cannot be scanned. A disadvantage of the prone position is that the breast is not easy to be fixed due to the flowing water, and the breast deformation can affect image reconstruction error during the scanning process. Another disadvantage is that the upper surface and lower surface of the water bag may form a reverberation, which leads to artifacts. In addition, the water immersion method has disadvantages, such as the thickness of the liquid (water) between the ultrasound probe and the tissue may affect image quality, region of interest may not be in the physical focus area, and bubbles produced by the rotating ultrasound probe in the water may affect the image quality.

The direct contact method can be further classified into splint type and press down type. The splint type is similar to a molybdenum target splint type scanning method, wherein the mammary gland of the patient is held and fixed by two splints from two sides. A contact surface of one of the splints contacting the mammary gland is an acoustic plane. The ultrasound probe can move along the contact surface in the splint at a constant speed and scan the breast. Some disadvantages of the splint type scanning may include: a scanning position is different with an operation position, the peripheral mammary gland cannot be scanned, the patient feels uncomfortable, and it is not suitable for patients with small breasts.

The press down type of the direct contact method refers to when the ultrasound probe covers the breast of a patient in a supine position, or refers to when a patient stands and moves her breast to press the ultrasound probe, wherein the ultrasound probe's scanning surface is orientated upward. The characteristic of the press down type is suitable for thin and small people, and the scanning position is identical to the operation position such that the patient does not need to change the position to continue an automated whole breast scanning after a hand-held probe scanning.

The press down type is the most widely used method. A commercialization implementation thereof is using porous net cloth to cover the mammary gland tissues and the ultrasound probe scanning on the net cloth.

However, the current press down type automated mammary gland scanning method has certain disadvantages.

For example, as the reconstruction is performed after mechanical scanning, if some area has pool contact with the body tissue and is separated by air, a shadow will be generated and thus will seriously affect the quality of the images. Because the scanning time is usually long, whether the contact situation is desirable cannot be known in advance, so the success rate of data collecting will be affected.

SUMMARY

Aiming at the above-described drawbacks in the prior art, ultrasound imaging devices and methods are provided in this disclosure.

According to one embodiment of the present disclosure, an ultrasound imaging method is provided. The ultrasound imaging method includes: performing a first scanning to a target object by using an ultrasound transducer of the ultrasound probe assembly at a first speed to obtain first ultrasound signals, wherein the ultrasound probe assembly includes an acoustic window, and at least a part of a lower surface of the acoustic window contacts with the target object; determining a quality of the first scanning according to the first ultrasound signals; scanning the target object by using the ultrasound transducer at a second speed to obtain second ultrasound signals, and acquiring a second ultrasound image of the target object according to the second ultrasound signals; and displaying the second ultrasound image.

According to one embodiment of the present disclosure, an ultrasound imaging device is provided. The ultrasound imaging device may include an ultrasound probe assembly, a signal processor and a display.

The ultrasound probe assembly may include a housing, an acoustic window disposed at the bottom portion of the housing and of which at least a part of a lower surface may contact with a target object, an ultrasound transducer disposed above the acoustic window and configured to scan the target object, and an ultrasound transducer driving mechanism which may be connected with the ultrasound transducer and may drive the ultrasound transducer at a first speed to perform a first scanning to the target object to obtain first ultrasound signals.

The signal processor may receive and analyze the first ultrasound signals to determine a quality of the first scanning according to the first ultrasound signals, where the ultrasound transducer driving mechanism may further drive the ultrasound transducer at a second speed to perform a second scanning to the target object to obtain second ultrasound signals based on the analysis of the first ultrasound signals, and the signal processor may further receive the second ultrasound signal and generate a second ultrasound image based on the second ultrasound signals.

The display may display the second ultrasound image.

BRIEF DESCRIPTION OF THE DRAWINGS

For illustrating embodiments of this disclosure or technical solutions in the prior art more clearly, some figures for describing the embodiments or the prior art will be briefly described below. It is apparent that the figures in the following descriptions are only some examples of this disclosure. The ordinary skilled person in the art can obtain other figures according to these figures without contributing any creative efforts or new matter based on this disclosure.

DETAILED DESCRIPTIONS

Figure 1:
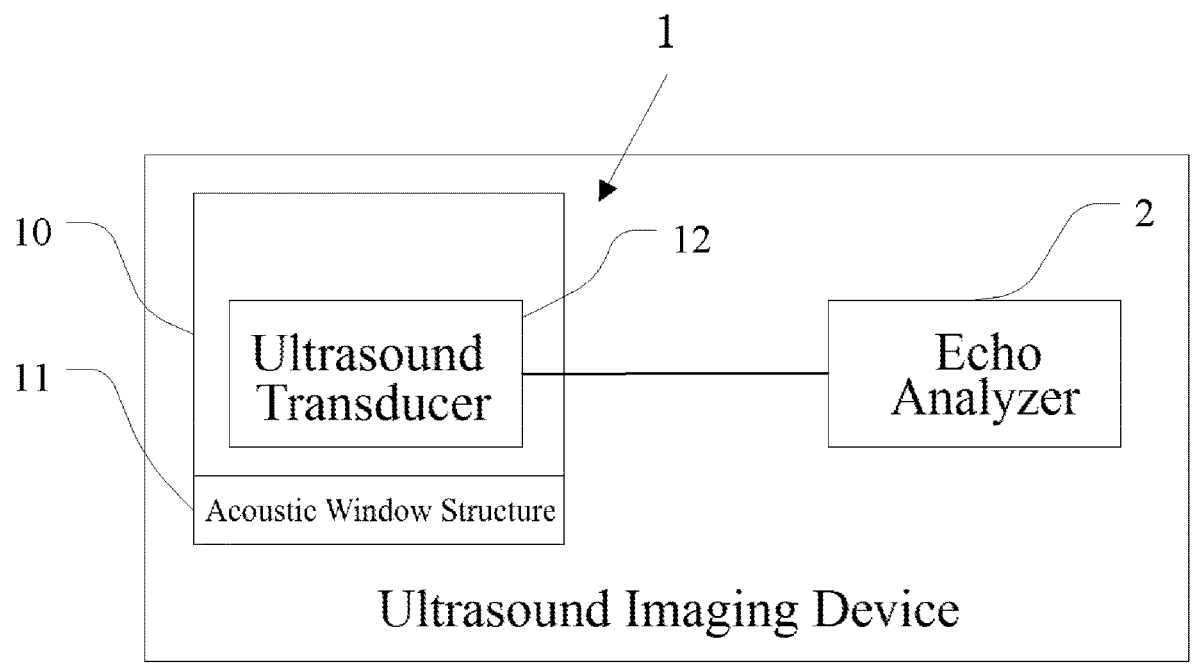
FIG. 1 is a schematic diagram illustrating a structure of a 3D ultrasound imaging device according to a first embodiment of the present disclosure.

In view of the problems in the prior arts, such as the discomfort of the patient caused by the mechanical movement of the probe and low success rate of data collecting, at least one embodiment of the present disclosure provides a new ultrasound imaging technology. According to one embodiment of the present disclosure, an ultrasound imaging device can employ a housing to encapsulate a mechanical probe, and a unique process of high-speed pre-scanning may ensure good contact of probe surface with the patient. Meanwhile, the mechanical movement may not be applied to body tissues directly, thus both the patient and the physician may have a better experience.

In some embodiments, an ultrasound imaging method is provided. The method may include:

performing a first scanning to a target object by using an ultrasound transducer of an ultrasound probe assembly at a first speed to obtain first ultrasound signals, wherein the ultrasound probe assembly comprises a acoustic window, and at least a part of a lower surface of the acoustic window contacts with the target object;

determining a quality of the first scanning according to the first ultrasound signals;

scanning the target object by using the ultrasound transducer at a second speed to obtain second ultrasound signals, and acquiring a second ultrasound image of the target object according to the second ultrasound signals; and displaying the second ultrasound image.

In some embodiments, determining a quality of the first scanning according to the first ultrasound signals may include generating a first ultrasound image according to the first ultrasound signals and displaying the first ultrasound image.

In some embodiments, determining a quality of the first scanning according to the first ultrasound signals may include extracting a characteristic quantity from the first ultrasound signals, categorizing the first ultrasound signals according to the characteristic quantity extracted to obtain a category of the first ultrasound signals, and determining the quality of the first scanning according to the category of the first ultrasound signals.

In some embodiments, determining the quality of the first scanning according to the category of the first ultrasound signals may include generating a quality evaluation of the quality of the first scanning according to the category of the first ultrasound signals and displaying the quality evaluation of the quality of the first scanning.

In some embodiments, determining a quality of the first scanning according to the first ultrasound signals may also include comparing the first ultrasound signals with a pre-stored characteristic quantity and determining the quality of the first scanning according to a result of the comparison between the first ultrasound signals and the pre-stored characteristic quantity.

In some embodiments, performing a first scanning to the target object by using the ultrasound probe at a first speed may include:

a. scanning the target object by using the ultrasound probe at a first speed to obtain a first group of first ultrasound signals, and scanning the target object again by using the ultrasound probe at a first speed to obtain a second group of first ultrasound signals; or scanning a target area of the target object by using the ultrasound probe at a first speed to obtain a first group of first ultrasound signals, dividing the target area into a first area and a second area according to the first group of first ultrasound signals, and scanning the first area by using the ultrasound probe at a first speed to obtain a second group of first ultrasound signals.

In these embodiments, determining a quality of the first scanning according to the first ultrasound signals may include determining the quality of the first scanning according to the first and/or second group of first ultrasound signals.

In some embodiments, determining the quality of the first scanning according to the first and/or second group of first ultrasound signals may include generating a first ultrasound image according to the second group of first ultrasound signals and displaying the first ultrasound image.

In some embodiments, determining the quality of the first scanning according to the first and/or second group of first ultrasound signals may include extracting characteristic quantity from the second group of first ultrasound signals, categorizing the second group of first ultrasound signals according to the extracted characteristic quantity to obtain a category of the second group of first ultrasound signals, and determining the quality of the first scanning according to the category of the second group of first ultrasound signals.

In some embodiments, determining the quality of the first scanning according to the category of the second group of first ultrasound signals may include generating a quality evaluation of the quality of the first scanning according to the category of the second group of first ultrasound signals and displaying the quality evaluation of the quality of the first scanning.

In some embodiments, determining the quality of the first scanning according to the first and/or second group of first ultrasound signals may also include obtaining a first section image data in a pre-set plane from the first group of ultrasound signals, obtaining a second section image data in the pre-set plane from the second group of ultrasound signals, comparing the first section image data with the second section image data, and determining the quality of the first scanning according to the comparison between the first section image data and the second section image data.

In some embodiments, determining the quality of the first scanning according to the comparison between the first section image data and the second section image data may include generating a quality evaluation of the quality of the first scanning according to the comparison between the first section image data and the second section image data and displaying the quality evaluation of the quality of the first scanning.

In some embodiments, the first area may be an area where the acoustic window contacts with the target object and the second area may be an area where the acoustic window contacts with the air.

In some embodiments, the quality of the first scanning may include a contact degree between the acoustic window and the target object, a degree of bubble appearing in a first ultrasound image acquired by the first scanning and/or an image quality of the first ultrasound image acquired by the first scanning.

In some embodiments, the second speed may be slower than the first speed.

In some embodiments, the method may further include detecting a position of the ultrasound transducer relative to the acoustic window to acquire position information of the position of the ultrasound transducer relative to the acoustic window, and displaying the position information.

In some embodiments, an ultrasound imaging device is provided. The ultrasound imaging device may include an ultrasound probe assembly, a signal processor and a display.

The ultrasound probe assembly may include a housing, an acoustic window disposed at the bottom portion of the housing and of which at least a part of a lower surface may contact with a target object, an ultrasound transducer disposed above the acoustic window and configured to scan the target object, and an ultrasound transducer driving mechanism which may be connected with the ultrasound transducer and may drive the ultrasound transducer at a first speed to perform a first scanning to the target object to obtain first ultrasound signals.

The signal processor may receive and analyze the first ultrasound signals to determine a quality of the first scanning according to the first ultrasound signals, where the ultrasound transducer driving mechanism may further drive the ultrasound transducer at a second speed to perform a second scanning to the target object to obtain second ultrasound signals based on the analysis of the first ultrasound signals, and the signal processor may further receive the second ultrasound signal and generate a second ultrasound image based on the second ultrasound signals.

The display may display the second ultrasound image.

In some embodiments, the signal processor may include a first image processing unit which may receive the first ultrasound signals and generate a first ultrasound image according to the first ultrasound signals, and the display may further display the first ultrasound image.

In some embodiments, the signal processor may further include an echo analyzer. The echo analyzer may include a characteristic quantity extracting unit which may extract characteristic quantity from the first ultrasound signals, a categorizer which may categorize the first ultrasound signals according to the characteristic quantity extracted by the characteristic quantity extracting unit to obtain a category of the first ultrasound signals, and a quality determining unit which may determine a quality of the first scanning according to the category of the first ultrasound signals determined by the categorizer.

In some embodiments, the quality determining unit may further generate a quality evaluation of the quality of the first scanning according to the category of the first ultrasound signals from the categorizer, and the display may further display the quality evaluation of the quality of the first scanning.

In some embodiments, the ultrasound transducer driving mechanism may drive the ultrasound transducer at a first speed to scan the target object to obtain a first group of first ultrasound signals, and drive the ultrasound transducer at a first speed to re-scan the target object to obtain a second group of first ultrasound signals, and the signal processor may determine the quality of the first scanning according to the first and/or second group of first ultrasound signals.

In some embodiments, the signal processor may include an echo analyzer. The echo analyzer may include a section image acquiring unit which may generate a first section image data of a predetermined section according to the first group of first ultrasound signals and generate a second section image data of the predetermined section according to the second group of first ultrasound signals, a comparator which may compare the first section image data with the second section image data, and a quality determining unit which may determine the quality of the first scanning according to a comparison result of the comparator.

In some embodiments, the quality determining unit may further generate a quality evaluation of the quality of the first scanning according to the comparison result of the first section image data and the second section image data, and the display may further display the quality evaluation.

In some embodiments, the display may further include a sub-display unit which is disposed on the housing and displays a first ultrasound image obtained by the first ultrasound signals and/or the second ultrasound image.

In some embodiments, the ultrasound imaging device may further include a position indicator which monitors a position of the ultrasound transducer relative to the acoustic window to acquire a position information of the position of the ultrasound transducer relative to the acoustic window.

In some embodiments, in the ultrasound imaging device, the quality of the first scanning may include a contact degree between the acoustic window and the target object, a degree of bubble appearing in a first ultrasound image acquired by the first scanning and/or an image quality of the first ultrasound image acquired by the first scanning.

In some embodiments, in the ultrasound imaging device, the second speed may be smaller or slower than the first speed.

The ultrasound imaging device and method provided by embodiments of the present disclosure obtains ultrasound data by way of a pre-scanning (scanning at a first speed/the first scanning) performed by the ultrasound probe, to evaluate the quality of the contacting or coupling between the ultrasonic window surface of the probe and the body tissue, and then performs regular formal scanning after adjustment if necessary. Therefore the success rate of breast scanning can be improved.

According to one aspect of the present disclosure, one embodiment of the present disclosure provides an ultrasound imaging method which includes the following steps.

Step 1: Performing a first scanning with an ultrasound transducer of an ultrasound probe assembly at a first speed to obtain first ultrasound signals. In one embodiment of the present disclosure, besides the ultrasound transducer, the ultrasound probe assembly may further include an acoustic window. At least a part of the lower surface of the acoustic window contacts with a target object, that is, an object/a body to be examined. The target object can be any object applicable for ultrasound examination or scan, for example, human tissues or body tissue such as breast, animal tissues, etc.

In the embodiments of the present disclosure, the ultrasound probe assembly may have a detailed structure described in the following descriptions and the corresponding schematic diagrams, and also may have a detailed structure identical with that described in Chinese patent Application No. 201310351863.9, titled An ultrasound probe assembly, or Chinese patent Application No. 201310351756.6, also titled An ultrasound probe assembly, each of which applications and their translations are incorporated by reference in their entireties.

Step 2: Determining a quality of the first scanning according to the first ultrasound signals. In one embodiment of the present disclosure, the quality of the scanning (e.g. the first scanning herein) refers to a collection of any factors that affects the scanning process and/or the quality of the images acquired by the scanning and/or the final result of the scanning to the target object. For example, the quality of scanning may include, but not limited to, a contact degree between the acoustic window of the ultrasound probe assembly and the target object during the scanning, a degree of bubble appearing in the ultrasound image acquired by the scanning and/or the image quality of the ultrasound image acquired by the scanning, etc.

Step 3: Scanning the target object with the ultrasound transducer at a second speed to obtain second ultrasound signals, and generating a second ultrasound image according to the second ultrasound signals.

In Step 2, the quality of the first scanning may be determined according to the first ultrasound signals. A user may determine, according to the first ultrasound signals, whether it is necessary to adjust one or more working parameters (e.g. the position of the ultrasound probe assembly relative to the target object, the contact condition between the acoustic window assembly and the target object, the settings of imaging parameters, etc.) during the current scanning. For example, the user can determine whether it is necessary to adjust one or more working parameters according to the quality of the first scanning. If not necessary, then the user can maintain the working parameters; if necessary, then the user can adjust the related working parameter(s) according to the quality of the first scanning and practical needs.

Thereafter, scanning the target object with the ultrasound transducer at a second speed to acquire second ultrasound signals, and generating a second ultrasound image of the target object according to the second ultrasound signals.

In the embodiments of the present disclosure, the first scanning at the first speed may be a pre-scanning, which can be used to preliminarily judge the current working parameters and/or working environment and/or working status such as the position of the ultrasound probe assembly relative to the target object, the contact condition between the acoustic window assembly and the target object, or the settings of imaging parameters, so as to determine whether there is a need of an adjustment. Scanning at the second speed may be used as a normal scanning process to the target object for acquisition of formal ultrasound images such as B-mode images, blood flow images, contrast images, and/or spectrum images.

Step 4: Displaying the second ultrasound image. After acquisition of the second ultrasound image of the target object in Step 3, the second ultrasound image can be displayed on the display.

In one embodiment of the present disclosure, the step of determining a quality of the first scanning according to the first ultrasound signals includes: generating a first ultrasound image according to the first ultrasound signals and displaying the first ultrasound image. In this embodiment, besides acquiring the second ultrasound image, it further includes acquiring a first ultrasound image according to the first ultrasound signals and displaying the first ultrasound image, thereby enabling the user to determine the quality of the first scanning through observing the first ultrasound image.

In one embodiment of the present disclosure, the step of determining a quality of the first scanning according to the first ultrasound signals can include: comparing the first ultrasound signals with a pre-stored characteristic quantity;

and determining a quality of the first scanning according to a result of the comparison between the first ultrasound signals and the pre-stored characteristic quantity. In various embodiments, the pre-stored characteristic quantity can be a characteristic describing desired signal characteristics and/or image characteristics such as mean value, variation, and/or gradient. Those pre-stored characteristic quantities may be written in the ultrasound imaging device before leaving the factory, or stored in storage of the ultrasound imaging device automatically by the ultrasound imaging device or manually by a user before the ultrasound examination.

In another embodiment of the present disclosure, the step of determining a quality of the first scanning according to the first ultrasound signals may include: extracting characteristic quantity from the first ultrasound signals; categorizing the first ultrasound signals according to the characteristic quantity; and determining a quality of the first scanning according to a category of the first ultrasound signals. The details of this embodiment can be understood by referring to the examples described hereinafter.

In one embodiment of the present disclosure, the step of determining a quality of the first scanning according to the first ultrasound signals may include: generating a quality evaluation of the first scanning according to the category of the first ultrasound signals; and displaying the quality evaluation of the first scanning. The quality evaluation measures the quality of the first scanning and may refer to any identification or indication, qualitatively or quantitatively, of the quality of the scan, e.g. a numerical value, colors, graphs, lines, combination of lines, etc.

In another embodiment of the present disclosure, the step of performing the first scanning to the target object at a first speed includes: scanning the target object by using the ultrasound transducer at a first speed to obtain a first group of first ultrasound signals and scanning the target object again with the ultrasound transducer at the first speed to obtain a second group of first ultrasound signals; and the step of determining a quality of the first scanning according to the first ultrasound signal includes: determining a quality of the first scanning according to the first and second group of first ultrasound signals.

In other words, in this embodiment, during the first scanning, the ultrasound transducer scans the target object at least twice, and acquires at least the first group of first ultrasound signals and second group of first ultrasound signals. That is, the first ultrasound signals include at least two groups of ultrasound signals.

In another embodiment of the present disclosure, the step of performing a first scanning to the target object with the ultrasound transducer at a first speed may include: scanning the target object in a scanning area at a first speed by using the ultrasound transducer to obtain a first group of first ultrasound signals, dividing the scanning area into a first area and a second area according to the first group of first ultrasound signals, and scanning the first area by using the ultrasound transducer at a first speed to obtain a second group of first ultrasound signals; and the step of determining a quality of the first scanning according to the first ultrasound signals includes: determining a quality of the first scanning according to the first and second group of first ultrasound signals.

That is, in this embodiment, during the first scanning, the scanning area scanned by the ultrasound transducer at the first time (i.e. the area the ultrasound transducer sweeps across during the first scanning) is divided into two areas, and when performing the second scanning at the first speed, it may only be necessary to scan one of the at least two areas, and not the other one, which may not need to be scanned again. Therefore, it may enhance the speed of the first scanning and save time.

For example, in one embodiment of the present disclosure, the first area can be an area where the acoustic window contacts with the target object, while the second area can be an area where the acoustic window contacts with the air. So, during the second scanning at the first speed, only the first area need be scanned, rather than the second area.

In the aforementioned embodiments, the step of determining a quality of the first scanning according to the first and second group of first ultrasound signals may include: generating a first ultrasound image according to the second group of first ultrasound signals, and displaying the first ultrasound image. That is, besides the aforementioned generation of the second ultrasound image, the first ultrasound image is also generated according to the second group of first ultrasound signals and displayed, thereby allowing the user to determine the quality of the first scanning through observing the first ultrasound image.

In another embodiment of the present disclosure, the aforementioned step of determining a quality of the first scanning according to the first and second group of first ultrasound signals may include: extracting characteristic quantity from the second group of first ultrasound signals; categorizing the second group of first ultrasound signals according to the characteristic quantity; and determining a quality of the first scanning according to a category of the second group of first ultrasound signals. In this embodiment, the step of characteristic quantity extracting, the step of categorizing and the step of determining a quality of the first scanning according to a category are similar to the aforementioned embodiments and the similar embodiments described in detail below.

In another embodiment of the present disclosure, the step of determining a quality of the first scanning according to the category of the second group of first ultrasound signals may include: generating a quality evaluation of the first scanning according to the category of the second group of first ultrasound signals; and displaying the quality evaluation of the first scanning. Herein, the quality evaluation measuring the quality of the first scanning refers to any identification or indication that qualitatively or quantitatively describes the quality of the scanning, including a numerical value, colors, graphs, lines, combination of lines, etc.

In another embodiment of the present disclosure, the aforementioned step of determining a quality of the first scanning according to the first and second group of first ultrasound signals may include: obtaining a first section image data from the first group of ultrasound signals; obtaining a second section image data from the second group of ultrasound signals; comparing the first section image data with the second section image data; and determining a quality of the first scanning according to the comparison between the first section image data and the second section image data.

In another embodiment of the present disclosure, the aforementioned step of determining a quality of the first scanning according to the comparison between the first section image data and the second section image data includes: generating a quality evaluation of the quality of the first scanning; and displaying the quality evaluation. Herein, similar to the descriptions above, the quality evaluations measuring the quality refer to any identification or indication that qualitatively or quantitatively describes the quality of the scanning, including numerical values, colors, graphs, lines, combination of lines, etc.

In the aforementioned embodiments, the quality of the first scanning may include: a contact degree between the acoustic window and the target object, a degree of bubble appearing in the first ultrasound image acquired by the first scanning and/or an image quality of the first ultrasound image acquired by the first scanning, etc.

According to some embodiments of the present disclosure, the second speed is slower than the first speed, or the first speed is faster than the second speed. Therefore in some embodiments of the present disclosure, the first scanning may be a high speed scanning that is a pre-scanning at a higher speed compared to the second speed.

In another embodiment of the present disclosure, the aforementioned ultrasound imaging method further includes: detecting the position of the ultrasound transducer relative to the acoustic window to acquire position information representing position of the ultrasound transducer relative to the acoustic window, and outputting the position information. Herein, the position information can be outputted in any applicable type, for example, in visual style, through displaying on a display device (i.e. displaying on a sub-display unit disposed on the ultrasound probe assembly), or in other styles such as indicator light and sound.

In one embodiment of the present disclosure, an ultrasound imaging device is provided. The ultrasound imaging device includes: an ultrasound probe assembly, a signal processor and a display.

The ultrasound probe assembly may include:
a. a housing;
b. an acoustic window disposed at the lower surface of the housing, wherein at least a part of the acoustic window contacts with a target object;
c. an ultrasound transducer disposed above the acoustic window and configured to scan the target object; and
d. an ultrasound transducer driving mechanism connected with the ultrasound transducer and configured to drive the ultrasound transducer at a first speed to perform a first scanning to the target object to obtain first ultrasound signals.

The signal processor is configured to receive and analyze the first ultrasound signals to determine a quality of the first scanning according to the first ultrasound signals.

The ultrasound transducer driving mechanism is further configured to drive the ultrasound transducer at a second speed to perform a second scanning to the target object to obtain second ultrasound signals.

The signal processor is further configured to receive the second ultrasound signals and generate a second ultrasound image according to the second ultrasound signals.

The display is configured to display the second ultrasound image.

In one embodiment of the present disclosure, the signal processor includes a first image processing unit configured to receive the first ultrasound signals and generate the first ultrasound image according to the first ultrasound signals; and the display is further configured to display the first ultrasound image.

In other embodiments of the present disclosure, the signal processor includes an echo analyzer, which includes:
a characteristic quantity extracting unit configured to extract characteristic quantity from the first ultrasound signals;
a categorizer configured to categorize the first ultrasound signals according to the extracted characteristic quantity; and a quality determining unit configured to determine a quality of the first scanning according to a category of the first ultrasound signal.

In other embodiments of the present disclosure, the quality determining unit is further configured to generate a quality evaluation of the first scanning according to the category of the first ultrasound signal; and the display is further configured to display the quality evaluation.

In other embodiments of the present disclosure, the ultrasound transducer driving mechanism is configured to drive the ultrasound transducer at a first speed to scan the target object to obtain a first group of first ultrasound signals and drive the ultrasound transducer at a second speed to re-scan the target object to obtain a second group of first ultrasound signals; the processor is further configured to determine a quality of the first scanning according to the first and second group of first ultrasound signals.

In other embodiments of the present disclosure, the signal processor includes an echo analyzer, wherein the echo analyzer includes: a section image acquiring unit, configured to generate first section image data of a predetermined section according to the first group of first ultrasound signals and generate second section image data of the predetermined section according to the second group of first ultrasound signals; a comparator, configured to compare the first section image data with the second section image data; and a quality determining unit, configured to determine the quality of the first scanning according to the comparison result of the comparator.

According to one embodiment of the present disclosure, the quality determining unit is further configured to generate a quality evaluation of the quality of the first scanning according to the comparison result of the first section image data and the second section image data, and the display is further configured to display the quality evaluation.

In other embodiments of the present disclosure, the display further includes: a sub-display unit disposed on the housing and configured to display the first ultrasound image and/or the second ultrasound image.

In other embodiments of the present disclosure, the device further includes: a position indicator configured to monitor the ultrasound transducer's position relative to the acoustic window and acquire the position information of the ultrasound transducer's position relative to the acoustic window.

In other embodiments of the present disclosure, the position information can be displayed through the aforementioned display.

In other embodiments of the present disclosure, the position information can be displayed through the aforementioned sub-display unit.

In the aforementioned embodiments of the present disclosure, the quality of the first scanning includes: a contact degree between the acoustic window and the target object, or a degree of bubble appearing in the first ultrasound image acquired by the first scanning and/or an image quality of the first ultrasound image acquired by the first scanning.

In the aforementioned embodiments of the present disclosure, the second speed is slower than the first speed.

In one embodiment of the present disclosure, the aforementioned ultrasound imaging method can be a method of normal 2D ultrasound imaging, or method of 3D ultrasound imaging. And correspondingly, the ultrasound imaging device may be a 2D ultrasound imaging device or 3D ultrasound imaging device.

Some embodiments of the present disclosure are described in detail taking an example of a 3D ultrasound imaging method and device. It should be understood that these embodiments are only exemplary and should not limit the scope of the present disclosure.

Referring to FIG. 1, it is a schematic diagram illustrating a structure of a 3D ultrasound imaging device according to a first embodiment of the present disclosure.

The 3D ultrasound imaging device of the first embodiment includes an ultrasound probe assembly 1 and a signal processor, and the signal processor may include an echo analyzer 2.

The ultrasound probe assembly 1 may include:
a. a probe housing 10;
b. an acoustic window 11, which is located under and abutted against the probe housing 10 to form a sealed chamber, wherein the sealed chamber is filled with coupling oil, and surface of the acoustic window 11 contacts with the breast of the body to be examined; and an ultrasound transducer 12 which includes an acoustic head and a vertical shaft, wherein the acoustic head is immersed in the coupling oil in the sealed chamber, and the acoustic head moves back and forth repetitively at a first speed to pre-scan the breast of the body to be examined through the surface of the acoustic window 11, thus to obtain initial ultrasound signals.

It should be noted that, the acoustic window 11 may use acoustic window material having relative high mechanical strength, thus the mechanical movement of the ultrasound transducer 12 will not be applied to the body through the acoustic window 11, the acoustic window 11 will not produce deformation, and a scanning track of the probe is fixed. Therefore the collection process is stable, and can avoid a situation of "first tight and loosen afterwards" or "first loose and tight afterwards" due to inappropriate initial placement angle of the probe.

The echo analyzer 2 may be used to analyze the initial ultrasound signals obtained from the ultrasound transducer 12 to determine the quality of the ultrasound image acquired by the high-speed pre-scanning executed by the ultrasound transducer 12.

The ultrasound transducer 12 moves back and forth in the sealed chamber at a second speed to re-scan for obtaining ultrasonic signals.

The echo analyzer 2 will be further described in the following embodiments.

Figure 2:
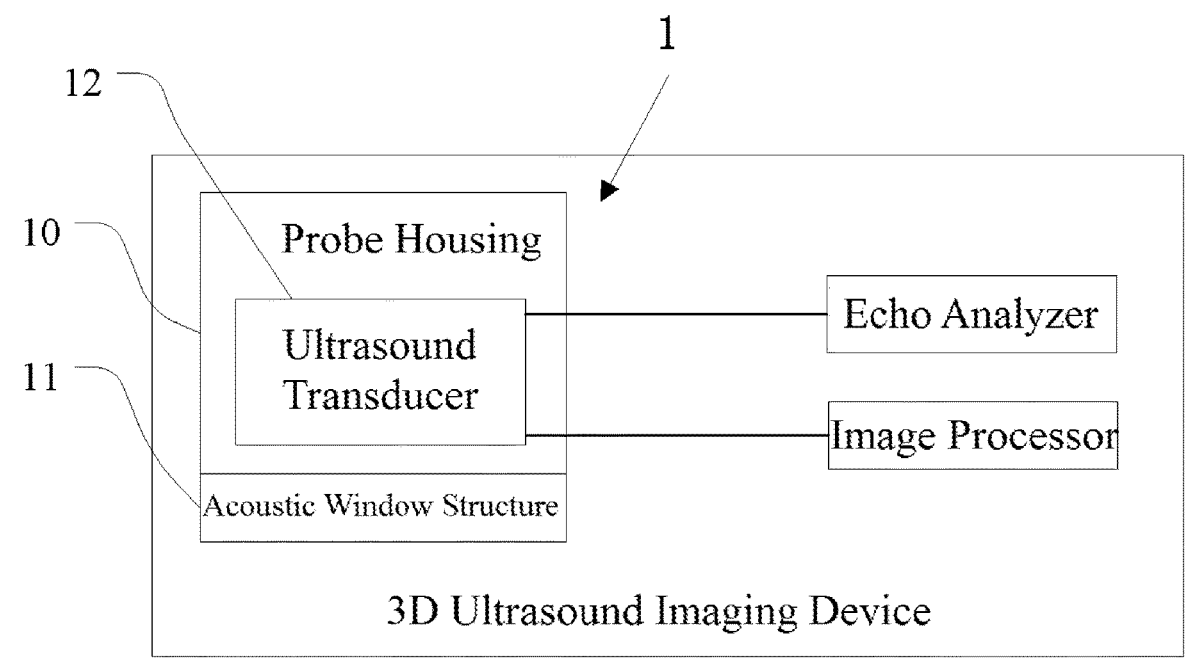
FIG. 2 is a schematic diagram illustrating a structure of a 3D ultrasound imaging device according to a second embodiment of the present disclosure.

Referring to FIG. 2, it is a schematic diagram illustrating a structure of a 3D ultrasound imaging device according to a second embodiment of the present disclosure.

Comparing to the first embodiment, the device according to the second embodiment further includes:

an image processor configured to process the ultrasound signals acquired by moving the ultrasound transducer back and forth repetitively at the second speed in the sealed chamber, and analyze the ultrasound signals collected at a depth and reconstruct a 3D coronal plane image.

Figure 3:
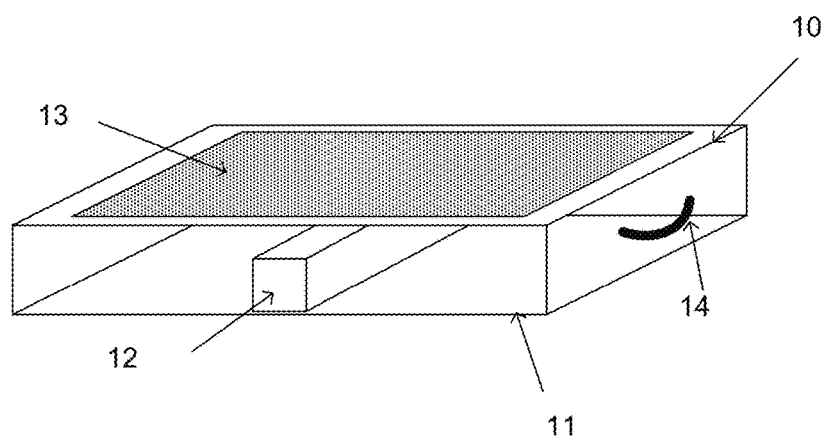
FIG. 3 is a schematic diagram illustrating a structure of an ultrasound probe assembly according to a first embodiment of a 3D ultrasound imaging device according to an embodiment of the present disclosure.

Referring to FIG. 3, it is a schematic diagram illustrating a structure of an ultrasound probe assembly according to a first embodiment of a 3D ultrasound imaging device according to an embodiment of the present disclosure.

The third embodiment will focus on a detailed structure of the ultrasound probe assembly 1 of the 3D ultrasound imaging device. The ultrasound probe assembly 1 may include:
a probe housing 10;
an acoustic window 11, which is located under and abutted against the probe housing 10 to form a sealed chamber, wherein the sealed chamber is filled with coupling oil, and surface of the acoustic window 11 contacts with the breast of the body to be examined; and an ultrasound transducer 12 which includes an acoustic head and an vertical shaft, wherein the acoustic head is immersed in the coupling oil in the sealed chamber, and the acoustic head moves back and forth repetitively at a first speed to pre-scan the breast of the body to be examined through the surface of the acoustic window 11, to obtain initial ultrasound signals; the ultrasound transducer 12 also can move back and forth repetitively at a second speed to perform a re-scanning to obtain ultrasound signals.

In this embodiment, a display unit 13 may be included at the top of the probe housing 10. The display unit 13 may be configured to display in real-time the initial ultrasound signals obtained by moving the ultrasound transducer 12 back and forth repetitively, and the 3D coronal plane image reconstructed by the image processor 3.

Optionally, a handle 14 may be located at one or both sides of the probe housing 10 of the ultrasound probe assembly 1 to facilitate the user's operation.

Figure 4:
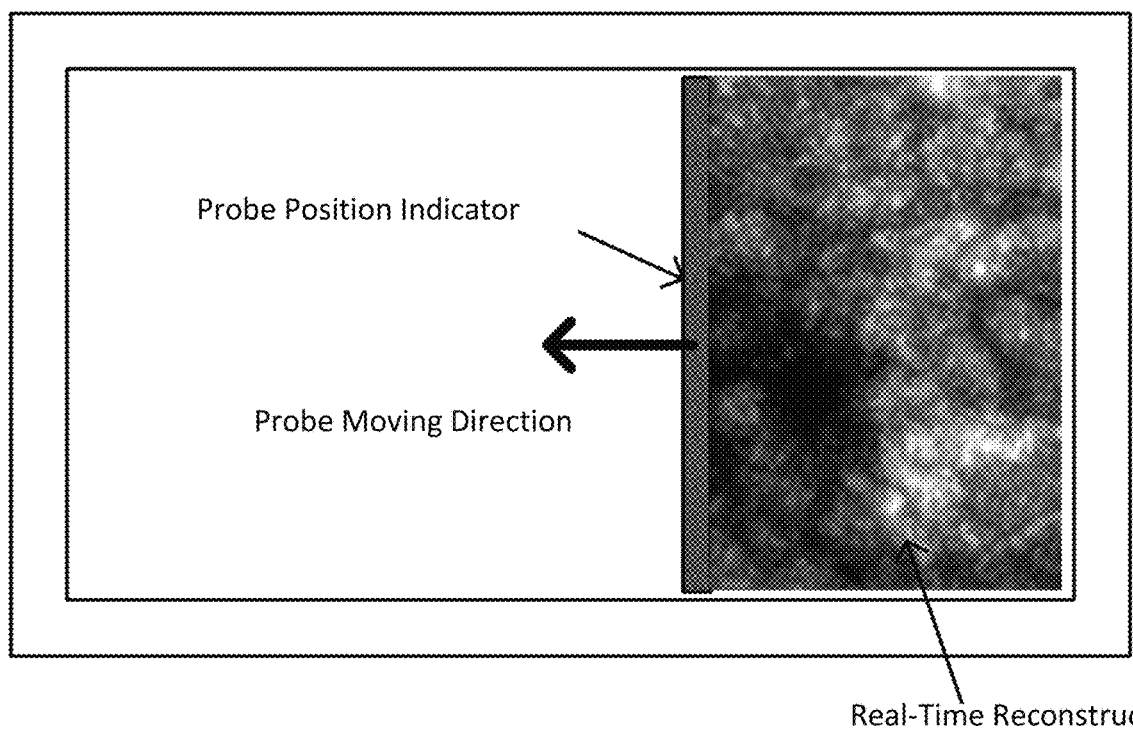
FIG. 4 is a schematic diagram illustrating location indication and real-time reconstruction during a data collection process by an ultrasound probe assembly of a 3D ultrasound imaging device according to an embodiment of the present disclosure.

The display unit 13 can be fixed to the top of the probe and corresponds to an actual scanning surface in a physical location. The user can know the scanning conditions of the probe through the display unit 13, which is similar to a "perspective" effect and more intuitive, as shown in FIG. 4.

Figure 5:
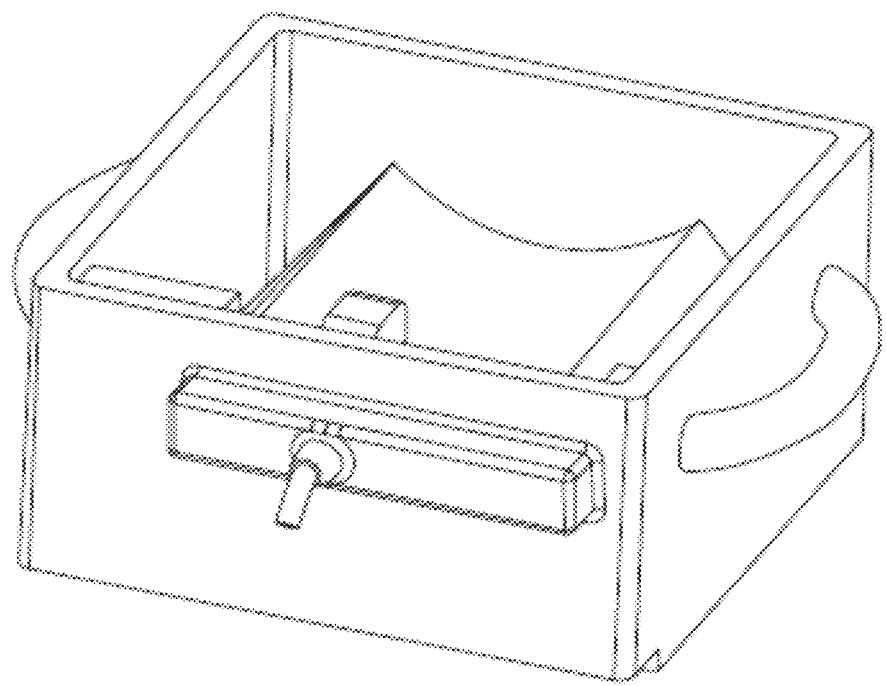
FIG. 5 is a schematic diagram illustrating a structure of an ultrasound probe assembly according to a second embodiment of a 3D ultrasound imaging device according to an embodiment of the present disclosure.
Figure 6:
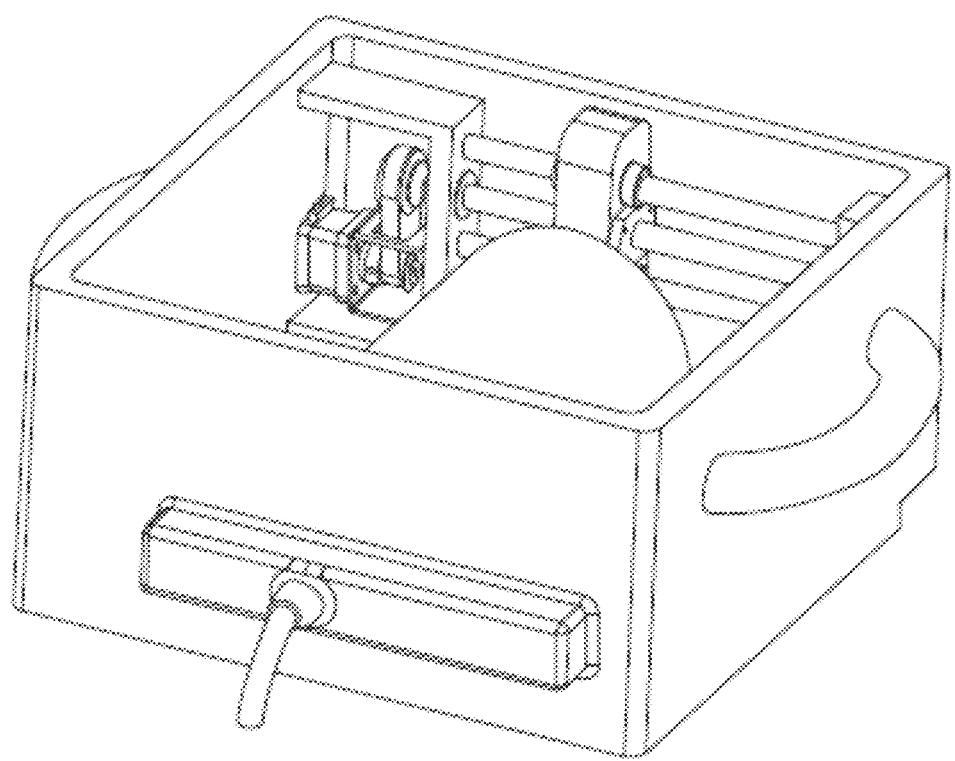
FIG. 6 is a schematic diagram illustrating a structure of an ultrasound probe assembly according to a third embodiment of a 3D ultrasound imaging device according to an embodiment of the present disclosure.

The surface of the acoustic window 11 is a plane in FIG. 3, but in other embodiments, the surface of the acoustic window 11 may also be an arc surface or a closed cylindrical shape, which can be shown as FIG. 5 and FIG. 6, and its working principles are similar and include the use of the ultrasound probe assembly shown in FIG. 3, thus will not be described in detail again.

Figure 7:
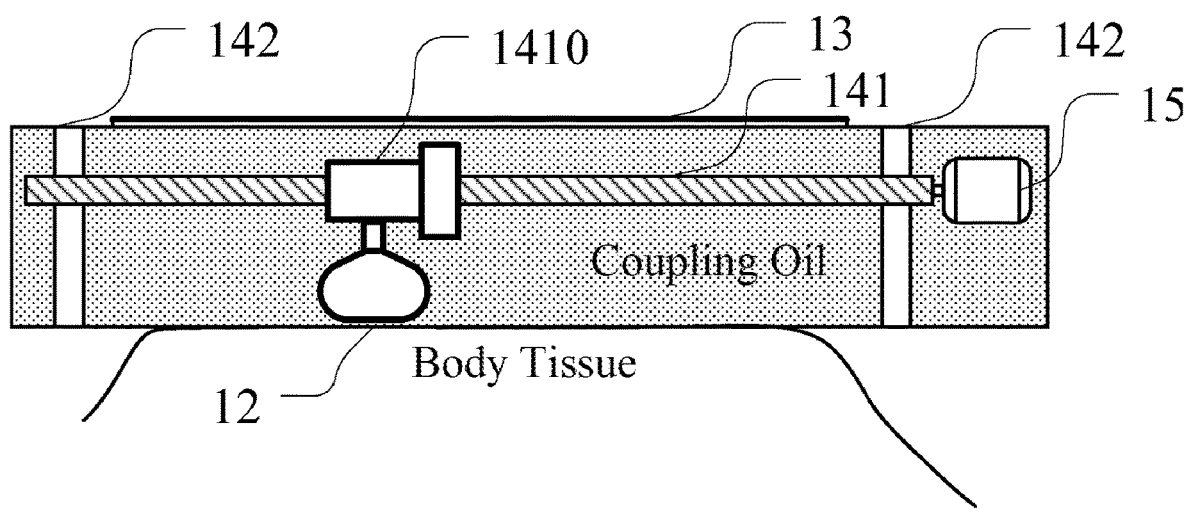
FIG. 7 is a schematic diagram illustrating a structure of an ultrasound probe assembly according to a fourth embodiment of a 3D ultrasound imaging device according to an embodiment of the present disclosure.

Referring to FIG. 7, it is a schematic diagram illustrating a structure of an ultrasound probe assembly according to a fourth embodiment of a 3D ultrasound imaging device according to an embodiment of the present disclosure.

FIG. 7 is a side view schematic diagram, and the ultrasound probe assembly of the fourth embodiment may further include:

a lead screw sliding rail formed by a lead screw 141 and two sliding rails 142, and a motor 15, wherein the lead screw 141 is connected to the vertical shaft of the ultrasound transducer 12 through a slider 1410; and the motor 15 pulls the lead screw 141 to move along the sliding rail 142 horizontally, and drives the ultrasound transducer 12 moving horizontally in the sealed chamber.

Figure 8:
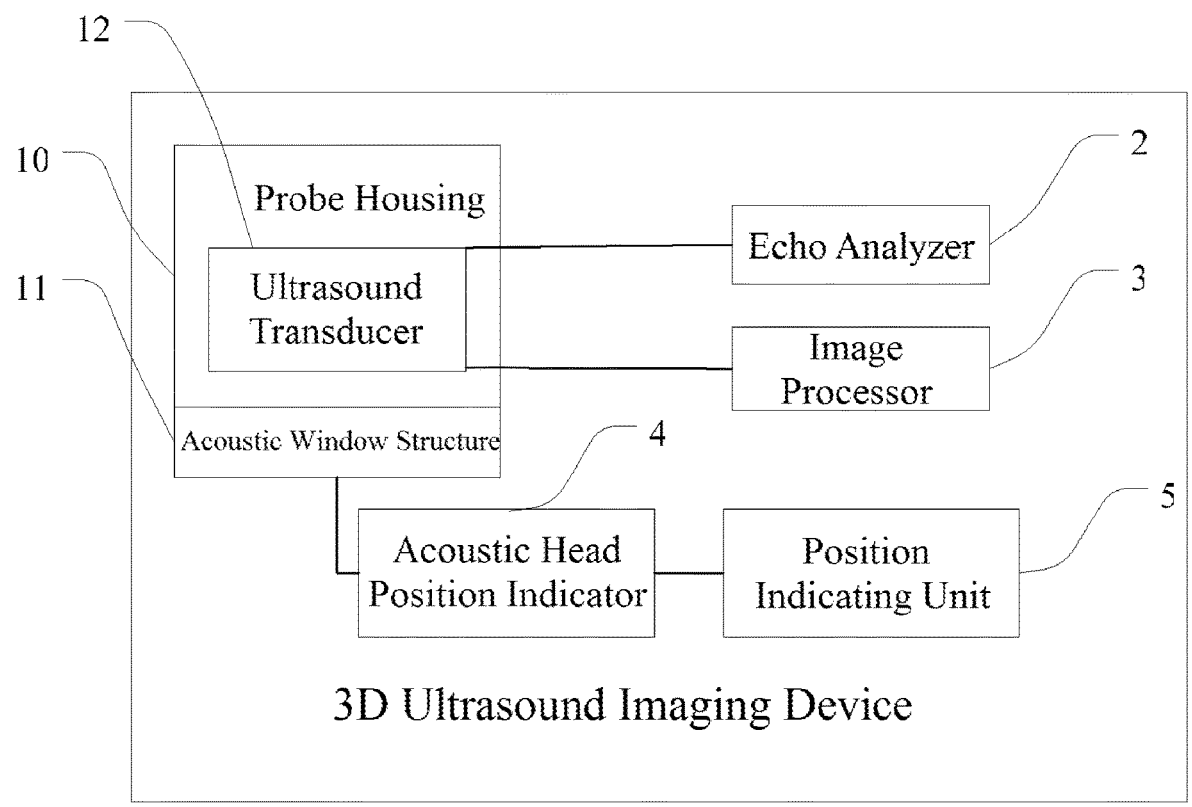
FIG. 8 is a schematic diagram illustrating a structure of an ultrasound probe assembly according to a fifth embodiment of a 3D ultrasound imaging device according to an embodiment of the present disclosure.

Referring to FIG. 8, it is a schematic diagram illustrating a structure of an ultrasound probe assembly according to a fifth embodiment of a 3D ultrasound imaging device according to an embodiment of the present disclosure.

The device of the fifth embodiment further includes:

An acoustic head position indicator 4 configured to monitor the position of the lead screw sliding rail and obtain position information of the acoustic head in the sealed chamber when the ultrasound transducer moves back and forth in the sealed chamber at the first speed or the second speed.

A position indicating unit 5 configured to label a current scanning position of the ultrasound transducer according to a received labeling instruction. Specifically, if the user stops collecting and restarts, or the user is interested in a certain ROI (Region Of Interest) of a newly collected image and intends to re-collect the region, he or he can enter instructions through a touch screen of the display unit 13, and then the position indicating unit 5 labels the region and the ultrasound probe assembly can re-collect the specific region.

In detailed implementations, the acoustic head position indicator 4 may be a resistance sensor, an inductive sensor, a rotary encoder or a proximity sensor. The mechanical movement of the slider 1410 can be converted to voltage or current through one of these sensors.

Figure 9:
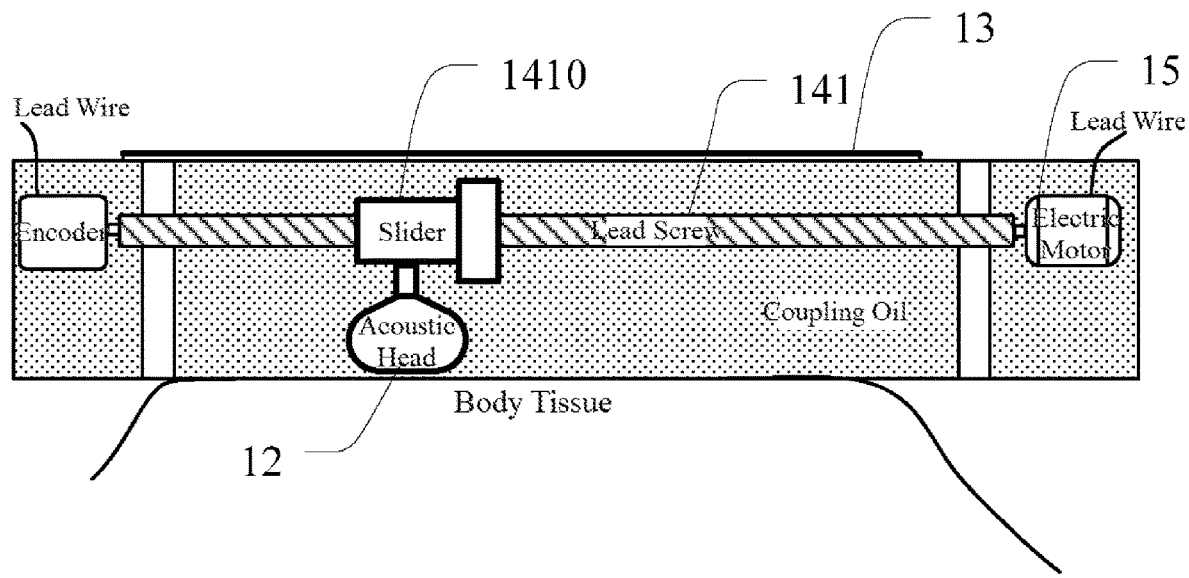
FIG. 9 is a schematic diagram illustrating a 3D ultrasound imaging device employing a rotary encoder to detect displacement of a slider according to an embodiment of the present disclosure.

Referring to FIG. 9, it employs a rotary encoder to detect displacement of the slider. The rotary encoder is linked with the lead screw, and can detect the quantity and direction of the displacement of the slider by using pulse of phase difference between two outputs.

Figure 10A:
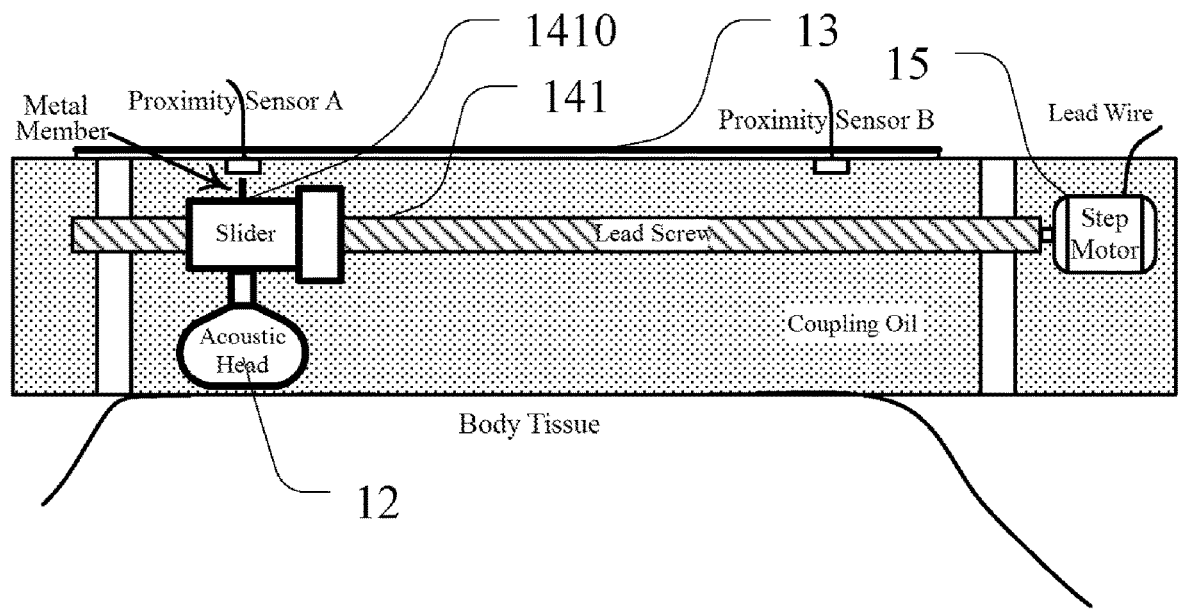
FIG. 10(a) and FIG. 10(b) are schematic diagrams illustrating a 3D ultrasound imaging device employing a proximity sensor to detect displacement of a slider according to another embodiment of the present disclosure.
Figure 10B:
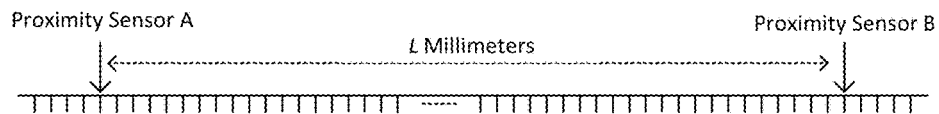

According to another embodiment, a proximity sensor may also be employed to realize the localization. A metal body may be fixed with the slider 1410 and move horizontally along with the ultrasound transducer, and the proximity sensor can be fixed to inner surface of the chamber. When the slider 1410 and the metal body move closely to the proximity sensor, the proximity sensor responds, and the response may be delivered to a processor through a lead wire. As shown in FIG. 10(*a*), two proximity sensors A and B may be mounted at two sides of a moving route of the ultrasound transducer. As shown in FIG. 10(*b*), assuming the two proximity sensors A's and B's positions are fixed, and a distance between them is L millimeters. The slider moves D millimeters with each pulse of the stepper motor, assuming that n=L/D, that is, the slider moves from a position A to a position B over n steps.

When using proximity sensor and step motor for localization, the entire moving route can be quantified according to a single step displacement d millimeter of the slider. Assuming the entire moving route is in (m>=n), and the sensor position A and B are located at position K1 and K2. It can count according to pulse number of the step motor during the movement of the slider. When the slide passes A, the proximity sensor acts and an internal count value should be K1. If it is not equal to K1, that means the localization has an error and needs to be corrected. A similar correction also can be applied to the position B.

It can be understood from the above description that, when using two proximity sensors, each time the slider returns, two iterations of correction may be performed, but when using only one proximity sensor, each time the slider returns, one time of correction may be performed.

The following will focus on the implementation of the echo analyzer 2.

When an acoustic window with greater area is moved to contact with the body, it is possible that the contact is not good due to angle and location; therefore the angle and position need to be adjusted. The technology in the prior art needs to complete the whole 3D data collection to know where the contact is not good, so that the success rate of a single data collection is reduced.

Generally speaking, three situations may occur during the scanning process of the ultrasound probe assembly:

A, contacts with air or minor coupling agent;
B, only contacts with major coupling agent; and
C, has good coupling with the human body.

Physicians do not want to see situations A and B, so when A or B occurs, they need to adjust to situation C to start a normal data collection.

A function of the echo analyzer 2 provided by the present disclosure is to identify these three situations A, B and C.

Figure 11A:
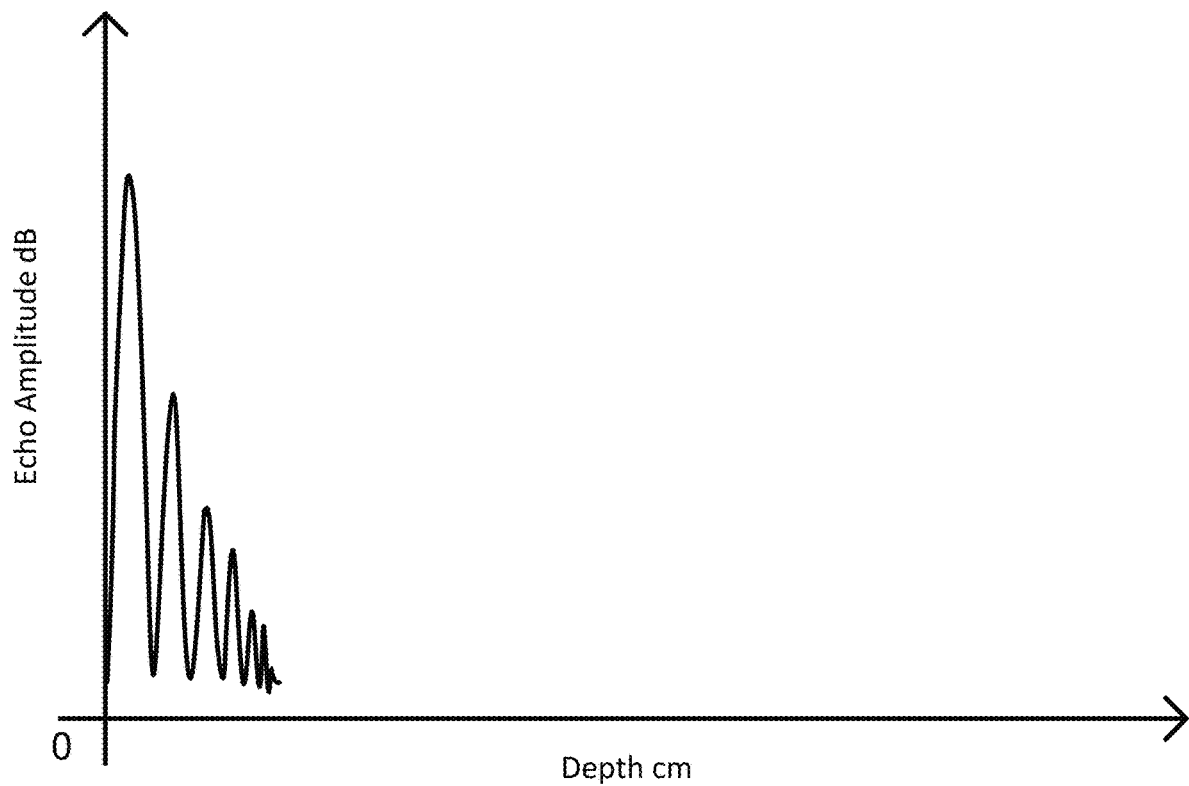
FIG. 11(a), FIG. 11(b) and FIG. 11(c) are schematic diagrams of echo signals obtained when an ultrasound probe assembly of a 3D ultrasound imaging device contacts with a different medium.
Figure 11B:
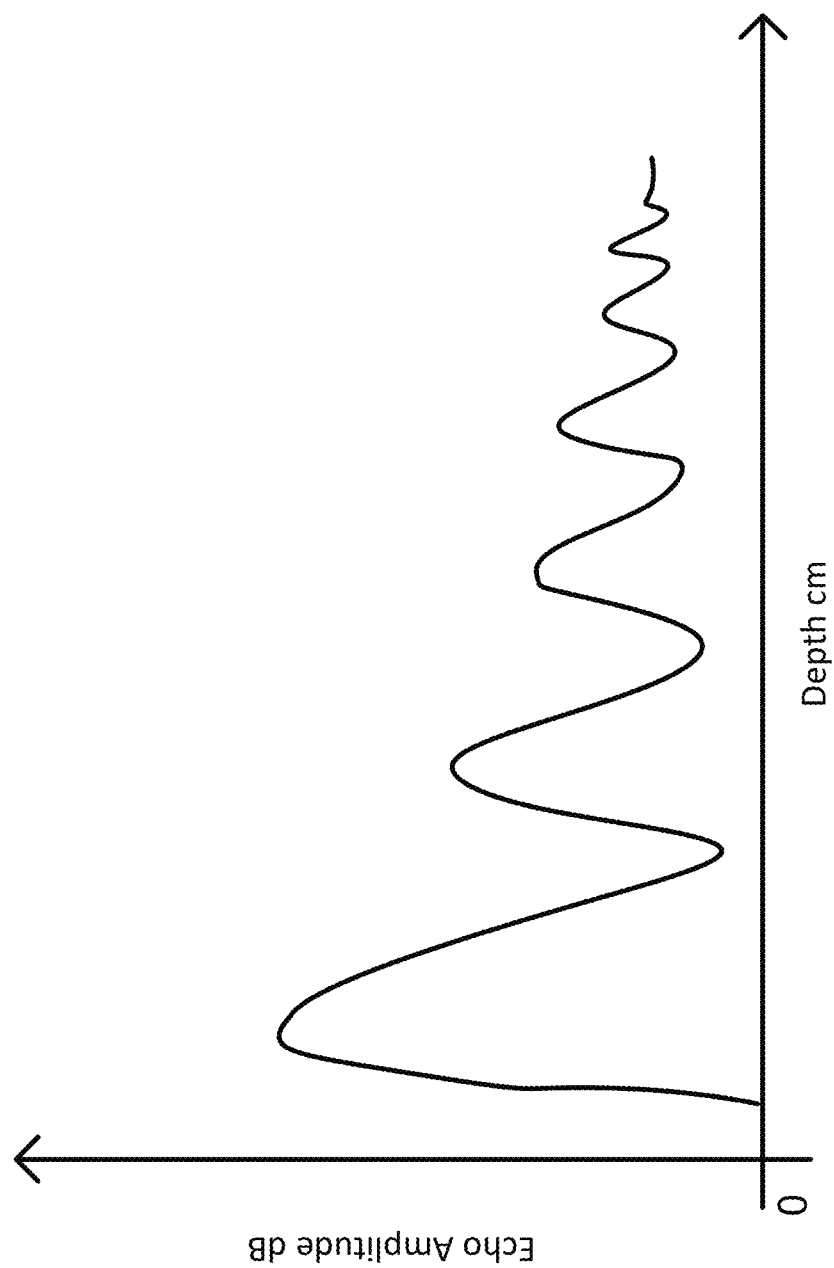
Figure 11C:
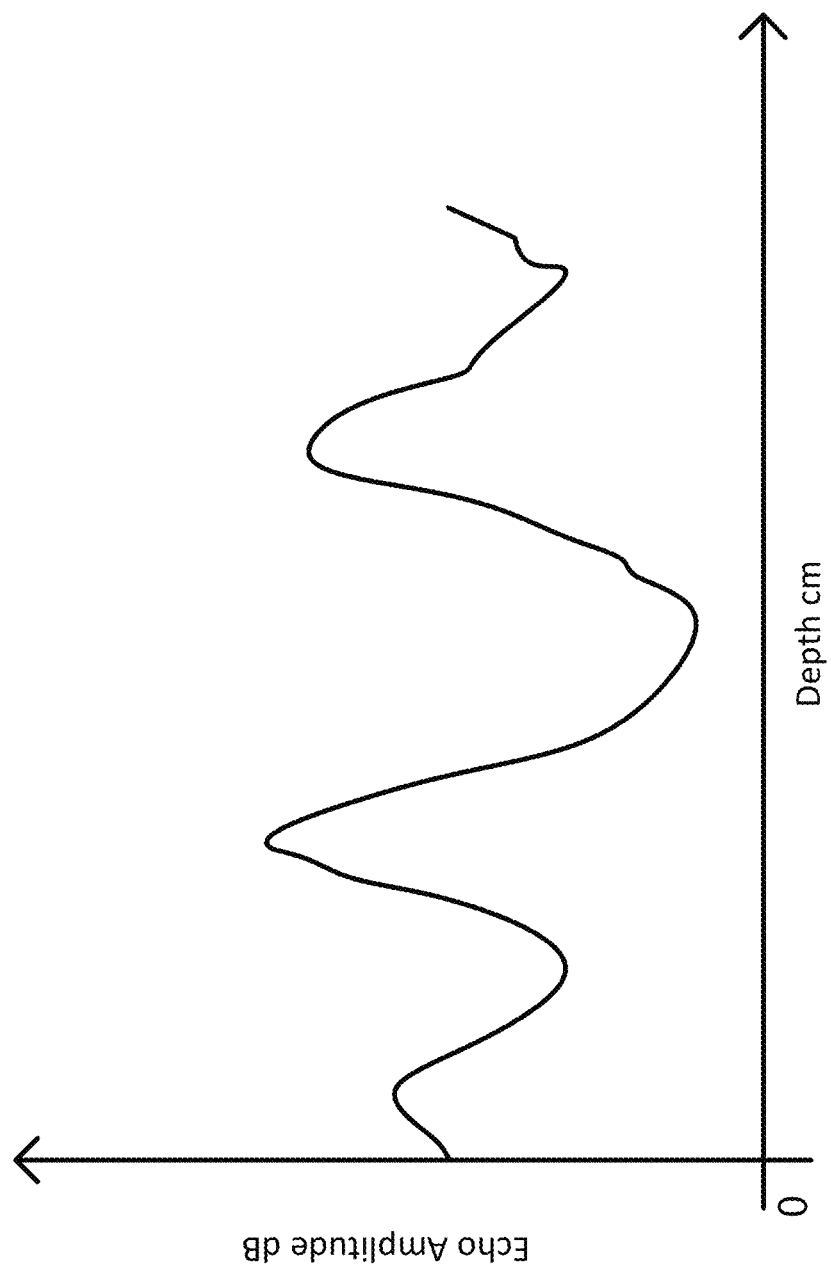
Figure 12:
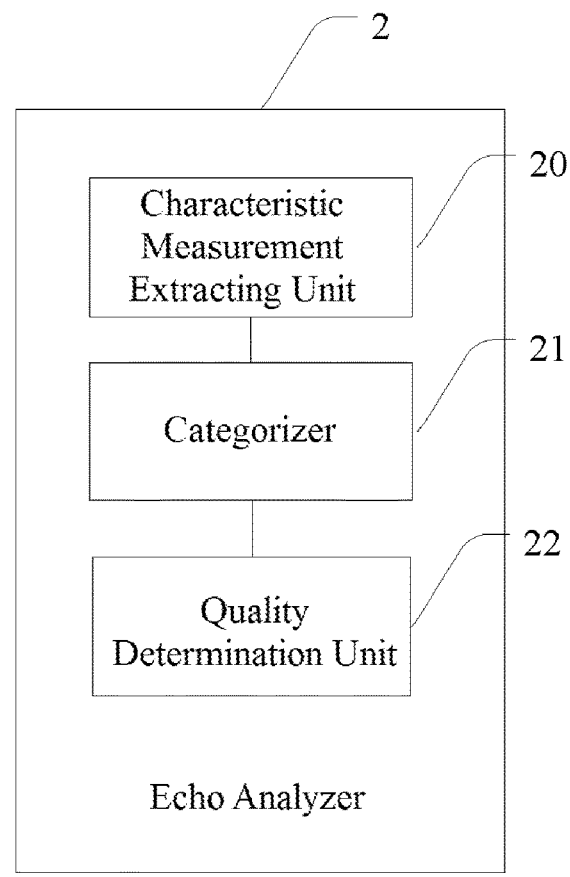
Figure 13:
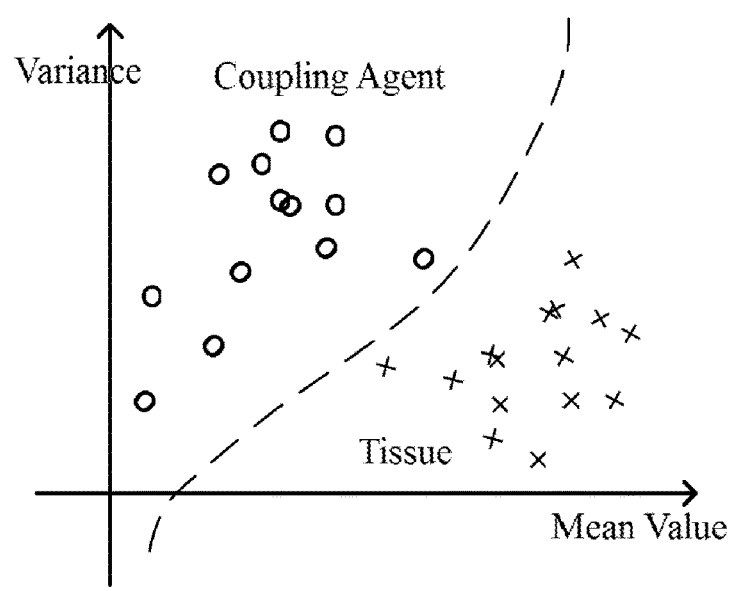

When the ultrasound probe assembly (hereinafter referred to as the probe) of the acoustic window directly exposed to the air or a very small amount of the coupling agent, the ultrasound signals received by the probe (hereinafter referred to as the echo) can be shown as FIG. 11(*a*). The near field echo vibrates periodically but decays rapidly due to reverberation of the surface of the probe. At this time, the characteristic of the echo is: the echo has certain strength within certain near field range, with the increase of the depth, the strength decays rapidly, with the increase of the depth, and a near field artifact disappears, which is close to a noise background of an unloaded probe.

When there is a great amount of coupling agent on the probe, and the coupling agent has no contact with the human body, the ultrasonic wave will be reflected many times in the range of the thickness of the coupling agent, thus forming the reverberation. As the coupling agent brings small attenuation to the ultrasonic wave, the near field echo of the echo is weak, and arrives at irregular interfaces between the coupling agent and the air to form a stronger echo, and then retracts to form the reverberation. The reverberation will propagate a long distance, thus the strength of a far field echo is uniform, the variance decays gradually, as shown in FIG. 11(*b*).

When the probe is in contact with the human body, as the body tissue is complex, the regularity of the echo is not as good as the two cases described above, as shown in FIG. 11(*c*). In this case, hyperechoic echo may appear in the near field skin layer, a plurality of hyperechoic spots may exist in the depth under the skin layer, or may decay rapidly after a hyperechoic spot, and the variance of the echo is majorly large.

A basic method of distinguishing the above three cases can be described as follows:

(1) Medium echo exists in the near field, and attenuates rapidly in the form of oscillation, so there is a great possibility that the probe contacts with the air directly;

(2) A layer of hypoechoic echo area exists in the near field (echo of the coupling agent), and may include a hyperechoic spot, strong echo appears subsequently and attenuates in the form of oscillation slowly, thus it is more likely that there is a great amount of coupling agent and does not contact with the human body. Because the coupling agent interface forming the reverberation is irregular, the echo signal amplitude becomes more uniform after several times of reflection; and (3) Medium echo exists in the near field (echo of the skin layer), and without the above-described characteristics of (1) and (2), the variance of the echo is relatively large, so there is a great possibility that the probe contacts well with the body.

When distinguishing these situations, it may be helpful to analyze the characteristic of the echo for categorization. The categorization is not limited to either-or categorization. It allows for the introduction of the concept of "fuzzy" to define measurement of the contact quality. Assuming contacting well with the body is set to output indication 1, contacting with air directly is set to 0, and the other cases can be attributed between 0 and 1 according to a contact degree. The measurement may be displayed in the display unit 13 to guide the interactive operation of the physician. The mode of display of the measurement can be a gray level difference or distinguished by color.

When the probe directly contacts with the air or the coupling agent is inadequate, it can be judged easily by the echo analysis. Assuming the echo signal is almost fixed when the probe contacts with the air directly, which is represented by $E_{air}$, it can be judged according to match the similarity between an actual echo signal collected represented by E and the $E_{air}$. The similarity can be defined relating to distance, such as the Euclidean distance:

$$\text{AirSimilarity}(E, E_{air}) = 1/(E - E_{air})T(E - E_{air})$$

The greater the similarity, the greater the possibility of directly contacting with the air.

It is difficult to distinguish the cases the coupling agent is plenty or contacts with the human body. In order to distinguish these kinds of situations, the characteristic of the echo may be extracted, and a first embodiment of the echo analyzer is provided in the present disclosure.

Figure 12:
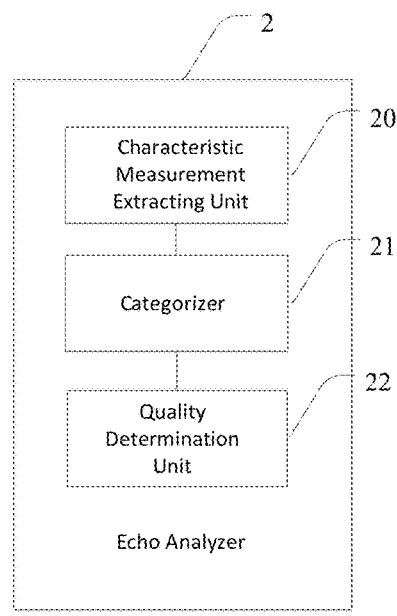
FIG. 12 is a schematic diagram of a structure of an echo analyzer according to a first embodiment of a 3D ultrasound imaging device according to embodiments of the present disclosure.

Referring to FIG. 12, it is a schematic diagram of a structure of an echo analyzer 2 according to a first embodiment of a 3D ultrasound imaging device according to embodiments of the present disclosure. The echo analyzer 2 includes:

a characteristic quantity extracting unit 20, configured to extract characteristic quantity from initial ultrasound signals obtained by the ultrasound transducer 12;

a categorizer 21, categorizing the initial ultrasound signals obtained by the ultrasound transducer 12 according to the extracted characteristic quantity obtained by the characteristic quantity extracting unit 20; and a quality determination unit 22, determining a contact degree between the breast of the body to be examined and an acoustic head of the ultrasound transducer 12 through the acoustic window 11, or a degree of bubble appearing in the ultrasound image according to a category output by the categorizer 21.

Wherein the characteristic quantity extracted by the characteristic quantity extracting unit 20 can be the Euclidean distance described above:

AirSimilarity($E$,Eair)=1/($E$-Eair)$T$($E$-Eair), or it can be near field echo characteristics SkinLayerMean and SkinLayerStd, or far field echo characteristic DetrendFarfieldStd.

Figure 13:
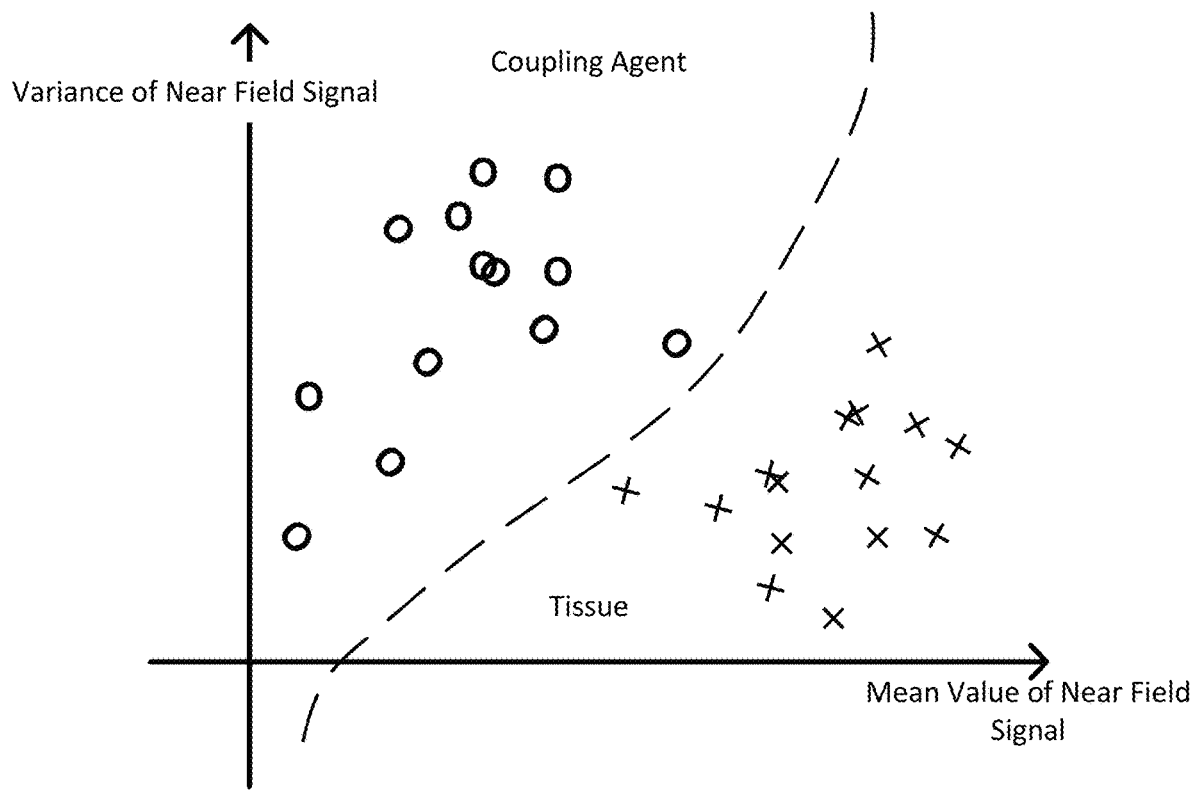
FIG. 13 is a diagram illustrating classification of an echo characteristic of a near field skin layer according to embodiments of the present disclosure.

One of the near field echo characteristics refers to: when the coupling agent is plenty, the near field attenuation is less and appears hypoechoic echo; the coupling agent may contain small bubbles, and appears as hyperechoic spot in the hypoechoic echo; overall speaking, it is low echo signal, large variance; in contrast, near field echo of the tissue is medium or hyperechoic and the signal distribution is relatively stable. As shown in FIG. 13, the horizontal axis represents the mean value of the near field signal and the vertical axis represents the variance of the near field signal, the "o"s in FIG. 13 show that there are plenty of coupling agents on the surface of the probe surface that the mean value is relatively small, and the variance is relatively large; x represents the probe contacts with the body tissue and the coupling is good, the near field echo amplitude is relatively large and stable. The dotted line in the middle is a boundary between the two cases. Generally, data within 2~3 millimeters can be selected for data analysis, and the characteristic quantity can be written as:

SkinLayerMean, SkinLayerStd,

Wherein the far field echo characteristic refers to: the reverberation formed by the low attenuation of the coupling agent will last for a relatively long time. The characteristic quantity of the far field echo may be variance of the mediate-far field echo; thus the amplitude variety of the far field reverberation of the coupling agent is relatively small. Because of the influence of internal gain, the mediate-far field echo may be analyzed through a time series to perform a detrending analysis; after that a calculated variance may more accurately reflect the characteristic. The detrend variance characteristic quantity of the far field echo can be recorded as (analyzing echo signals below a fixed depth, such as 2 cm to deeper regions):

DetrendFarfieldStd

As shown above, a characteristic vector of distinguishing the three types of situations/events can be recorded as:

$x$=[AirSimilarity,SkinLayerMean,SkinLayerStd,DetrendFarfieldStd]$T$

The characteristic quantity extracting unit 20 can further use principal component analysis or a depth learning method to extract characteristic quantity/value/vector from the initial ultrasound signals obtained by the ultrasound transducer 12.

Categorizer 21 establishes categorizing through the above four characteristic quantities and classifies the echo signals into three categories. It should be noted that the categorizer 21 may have a variety of embodiments of realization. For example, it can be a categorizer based on Bayesian statistics or a categorizer based on kernel function, or a categorizer supporting a vector machine.

First, a categorizer based on Bayesian statistics will be introduced in the following:

Counts a prior probability of occurrence of the three types of events, wherein a directly contacts with air, b has plenty of coupling agents and has no contact with the human body, and c contacts well with the human body. That is, probabilities of P(w=a), P(w=b) and P(w=c) can be calculated. It can be obtained through the user's random experimental statistics, such as statistics of area ratio of the three types of events when placed on the human body. For example, p(w=a)=0.35, p(w=b)=0.1, p(w=c)=0.55.

Calculates conditional probabilities p(x|w=a), p(x|w=b) and p(x|w=c). Calculation of the conditional probability also has strong operability, for example, calculates probability distribution of the characteristic vector x when the three types of events occur, by way of pre-set experiments and with the help of a visual.

Analyzes the current collected echo characteristic vector x and calculating posterior probability p(w=a|x), p(w=b|x) and p(w=c|x) of each type. Calculation formulas can be the following:

$p(w=a|x)=p(x|w=a)*p(w=a)/p(x)$, $p(w=b|x)=p(x|w=b)*p(w=b)/p(x)$, $p(w=c|x)=p(x|w=c)*p(w=c)/p(x)$.

Use a minimum error rate Bayesian categorizer to determine: choose a category having maximum posterior probability to complete the discriminant.

There are many other categorizers such as those based on Bayesian statistics or kernel function, which can realize the category through maximizing decision boundary. Or it may use a decision tree, multilayer feed forward neural network, etc., and will not be described in detail herein.

In addition, there is an echo analyzer which judges based on the current echo and the adjacent echo signals through analyzing a section image, for example, texture features of images in a certain region (there is a big difference between texture characteristics of the body tissue and the texture of coupling agent reverberation), which also can achieve the object of measurement.

Figure 14:
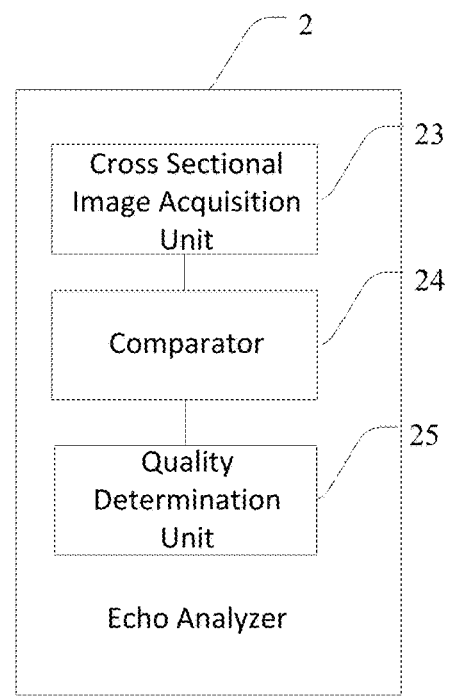
FIG. 14 is a schematic diagram of a structure of an echo analyzer according to a second embodiment of a 3D ultrasound imaging device according to embodiments of the present disclosure.

Specifically, referring to FIG. 14, it is a schematic diagram of a structure of an echo analyzer according to a second embodiment of a 3D ultrasound imaging device according to embodiments of the present disclosure, the echo analyzer including:

an image dividing unit or cross-sectional image acquisition unit 23 configured to acquire adjacent images of a section according to the initial ultrasound signal acquired by the ultrasound transducer 12;

a comparator 24 configured to compare the adjacent images of the section; and a quality determination unit 25 configured to determine a contact degree between the breast of the body to be examined and an acoustic head of the ultrasound transducer 12 through the acoustic window, or a degree of bubble appearing in the ultrasound image according to the comparison result of the comparator 24.

Directly displaying the image, or reconstructing and displaying a certain coronal plane in real-time, is another approach without utilizing scalar measurement. Although the image quality may be relatively poor, the user can roughly learn the present contact condition and estimate the expectation of the image quality.

As described above, the purpose of the echo analyzer 2 may be providing a quantitative indicator of the current image quality through the analysis of the ultrasound signal.

In one embodiment of the present disclosure, when a doctor is placing the ultrasound probe, it will not take a long time for the 3D ultrasound imaging device to acquire the entire 3D data. In one embodiment of the present disclosure, the employment of sparse sampling in data acquisition may significantly reduce the time consuming of the preparation during the placement of the ultrasound probe. In the present disclosure, when performing normal scan and 3D reconstruction, it may cost about 30 seconds to acquire about 200 frames of data within an area of 10 cm, i.e. 6-7 frames of data per second. During the detection of a contact condition, it is possible to finish scanning the entire data within 3 seconds, with a sampling rate of 15 frames per second and a total frame number of 45 in each scanning, i.e. 2-3 mm per frame. Such sampling frequency is relatively fast enough for the detection of a contact condition. Actually, during the detection, it is usually feasible to employ a higher pulse repetition rate in the detection, because there is no need for deeper echo data. Therefore the precision of the detection and the sampling rate may be further improved.

Figure 15A:
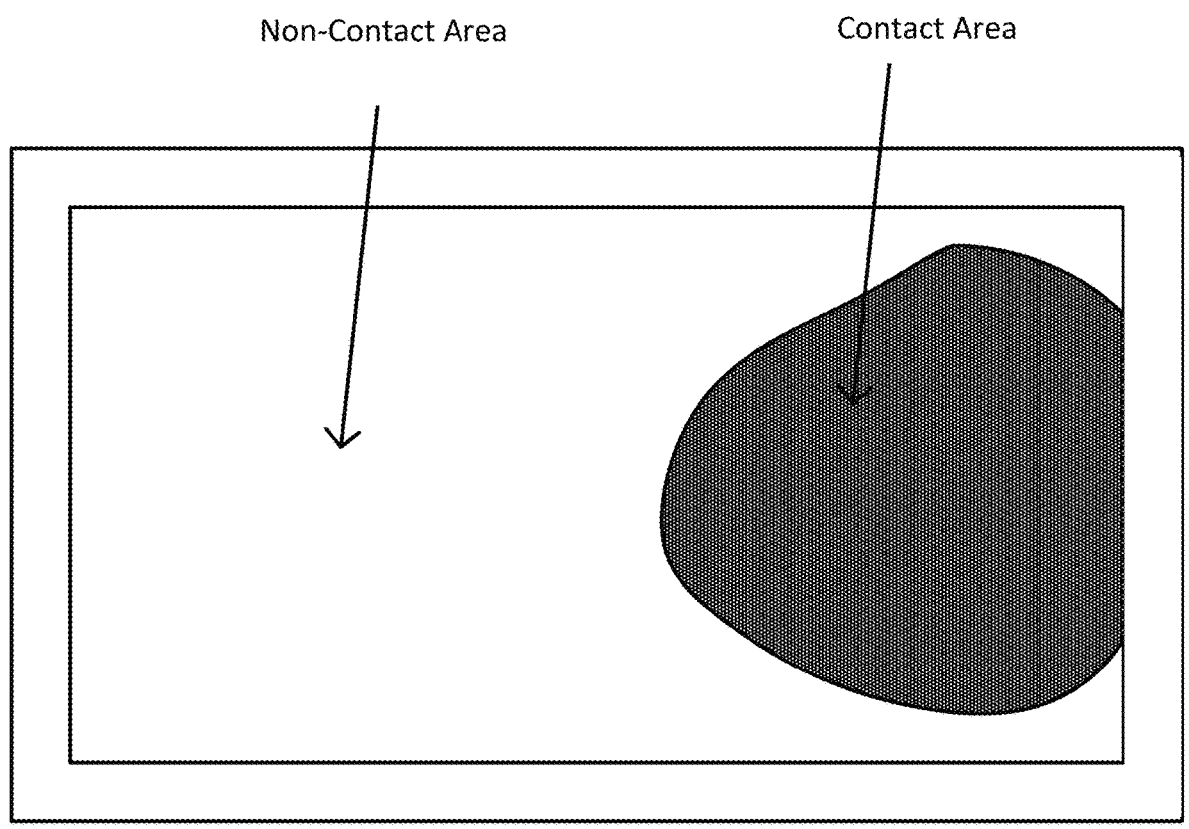
FIG. 15(a) and FIG. 15(b) are schematic diagrams of a contact effect indicator of a 3D ultrasound imaging device according to an embodiment of the present disclosure.
Figure 15A:
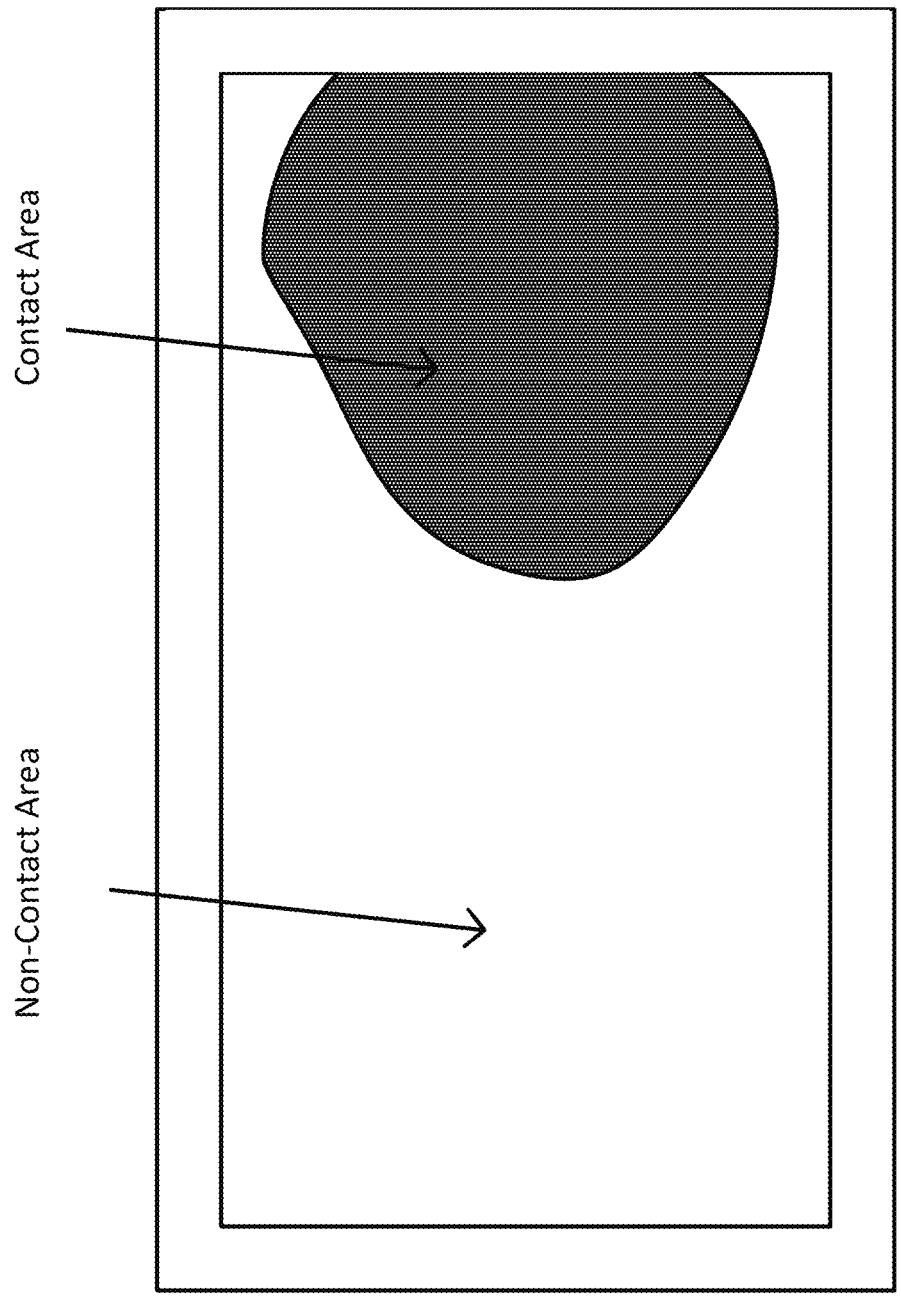
Figure 15B:
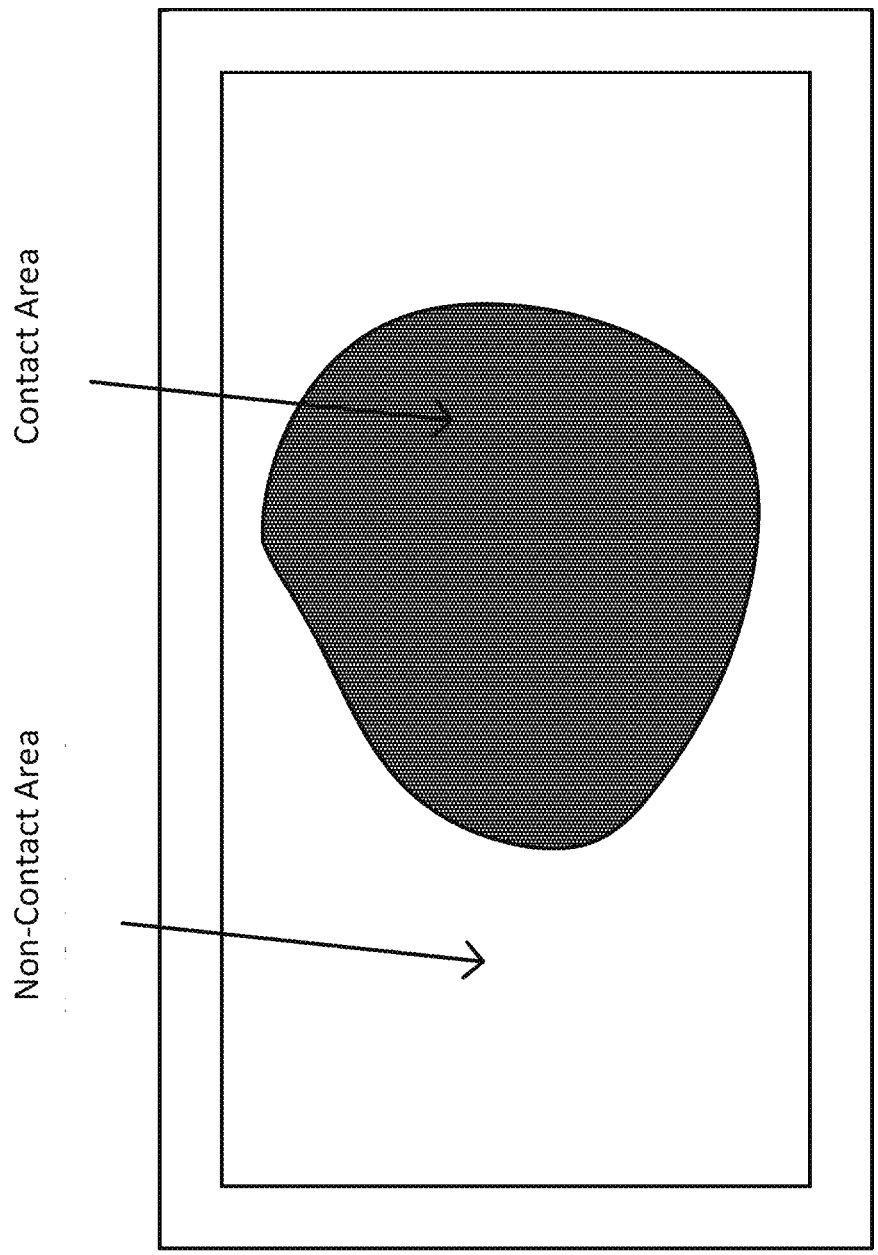

The ultrasound transducer repetitively collects data within the entire scanning plane at a relatively high speed, and displays the collection results analyzed and reconstructed on a screen of the display unit; thus the physician can observe a general morphology of the whole image in a short period from the screen and judge the pool contact regions, and can adjust the angle and position of the acoustic window of the probe in real-time to reach a best status. As shown in FIG. 15(a), the orientation of the probe is deflected to the left. After about 2-3 seconds of data collection, the echo analyzer of the 3D ultrasound imaging device analyzes the echo data, then judges and displays the contact area and noncontact area. The black area is a region where the probe contacts well with the tissue and the white area is a noncontact area. When the user observes the area, he or she can adjust the position of the probe to move to the left as shown in FIG. 15(b), and the position will be displayed to the user in the next 2-3 seconds.

Once the ultrasound signals are collected at a depth for coronal plane data collecting, for example, 1 cm, the computation of real-time 3D reconstruction is relatively small, because the computation is an incremental algorithm, the image has been reconstructed and does not need to be recalculated. When the user changes the depth or the effect, real-time 3D reconstruction might have to be updated to generate images from the collected data.

Correspondingly, the present disclosure also provides a 3D ultrasound imaging method which can be implemented by the above-described 3D ultrasound imaging device.

Figure 16:
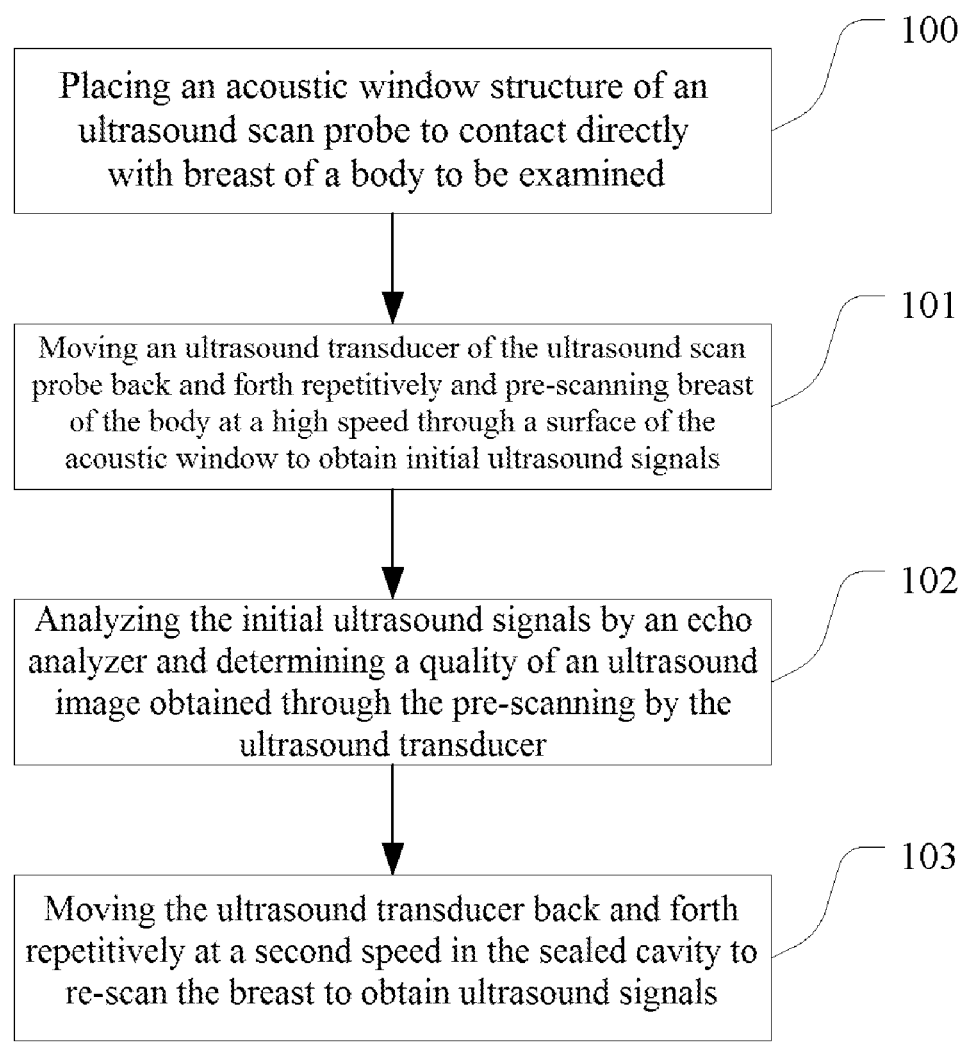
FIG. 16 is a schematic flow chart of a 3D imaging method according to a first embodiment of the present disclosure.

Referring to FIG. 16, it is a schematic flow chart of a 3D imaging method according to a first embodiment of the present disclosure. The method includes:

Step 100: placing an acoustic window of an ultrasound scan probe to contact directly with the breast of a body to be examined;

Step 101: moving an ultrasound transducer of the ultrasound scan probe in the sealed chamber back and forth repetitively and pre-scanning the breast of the body under examination at a high speed through a surface of the acoustic window to obtain an initial ultrasound signal;

Step 102: analyzing the initial ultrasound signal by an echo analyzer and determining a quality of an ultrasound image obtained through the pre-scanning by the ultrasound transducer; and Step 103: moving the ultrasound transducer repetitively back and forth in the sealed chamber at a second speed in the sealed chamber to re-scan the breast to obtain ultrasound signals.

Figure 17:
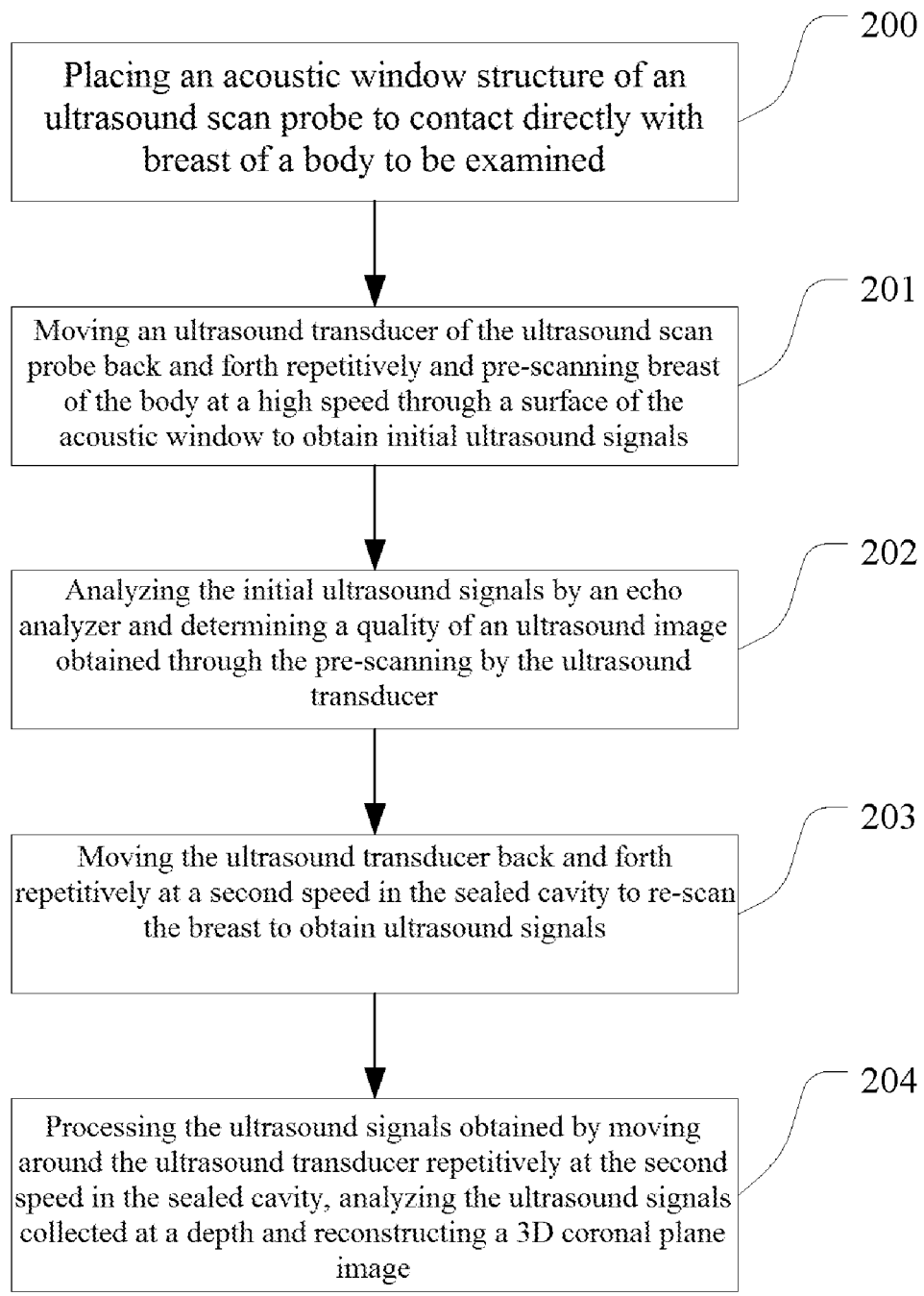
FIG. 17 is a schematic flow chart of a 3D imaging method according to a second embodiment of the present disclosure.

Referring to FIG. 17, it is a schematic flow chart of a 3D imaging method according to a second embodiment of the present disclosure, which includes:

Step 200: placing an acoustic window of an ultrasound scan probe to contact directly with the breast of a body to be examined;

Step 201: moving an ultrasound transducer of the ultrasound scan probe repetitively back and forth at a first speed in the sealed chamber and pre-scanning the breast of the body at a high speed through a surface of the acoustic window to obtain an initial ultrasound signal;

Step 202: analyzing the initial ultrasound signal by an echo analyzer and determining a quality of an ultrasound image obtained through the pre-scanning by the ultrasound transducer;

Step 203: moving the ultrasound transducer repetitively back and forth at a second speed in the sealed chamber to re-scan the breast to obtain ultrasound signals; and Step 204: processing the ultrasound signals obtained by moving around the ultrasound transducer repetitively at the second speed in the sealed chamber, analyzing the ultrasound signals collected at a depth and reconstructing a 3D coronal plane image.

Figure 18:
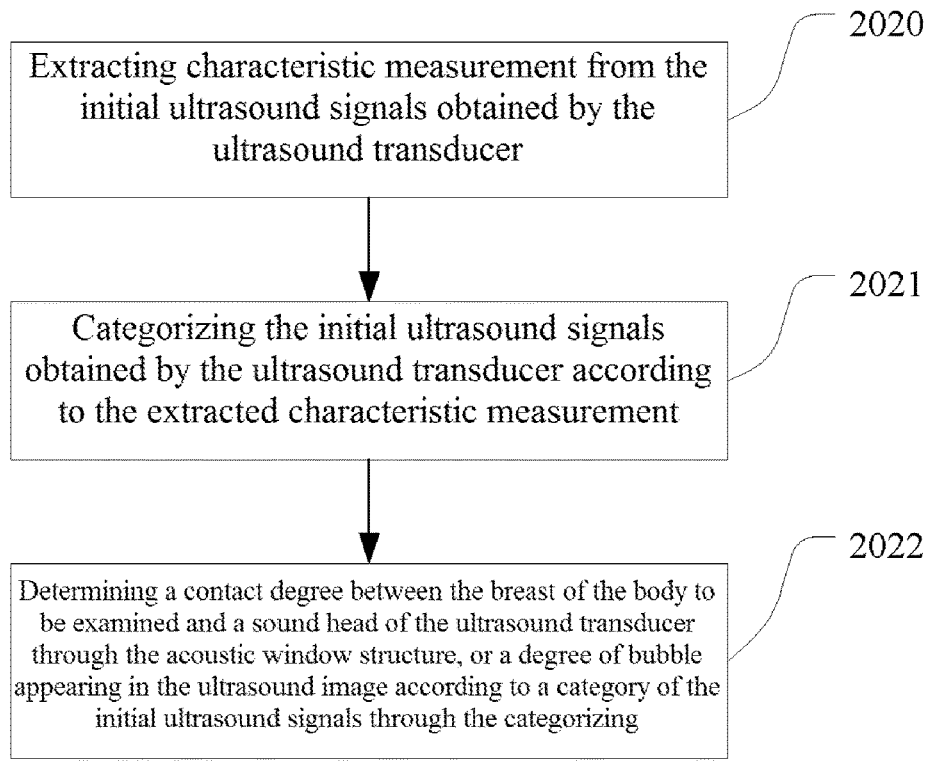
FIG. 18 is a schematic flow chart of a 3D imaging method according to a third embodiment of the present disclosure.

Referring to FIG. 18, it is a schematic flow chart of a 3D imaging method according to a third embodiment of the present disclosure, the third embodiment mainly describing a first method of echo analyzing by the echo analyzer. The method includes:

Step 2020: extracting a characteristic quantity from the initial ultrasound signal obtained by the ultrasound transducer;

Step 2021: categorizing the initial ultrasound signal obtained by the ultrasound transducer according to the extracted characteristic quantity; to be specific, one can utilize various categorizers to categorize the initial ultrasound signal acquired by the ultrasound transducer; the categorizers can be a Bayesian categorizer, categorizer based on kernel functions, categorizer supporting the vector machine, or the like; and Step 2022: determining a contact degree between the breast of the body to be examined and an acoustic head of the ultrasound transducer through the acoustic window, or a degree of bubble appearing in the ultrasound image according to a category of the initial ultrasound signal.

Figure 19:
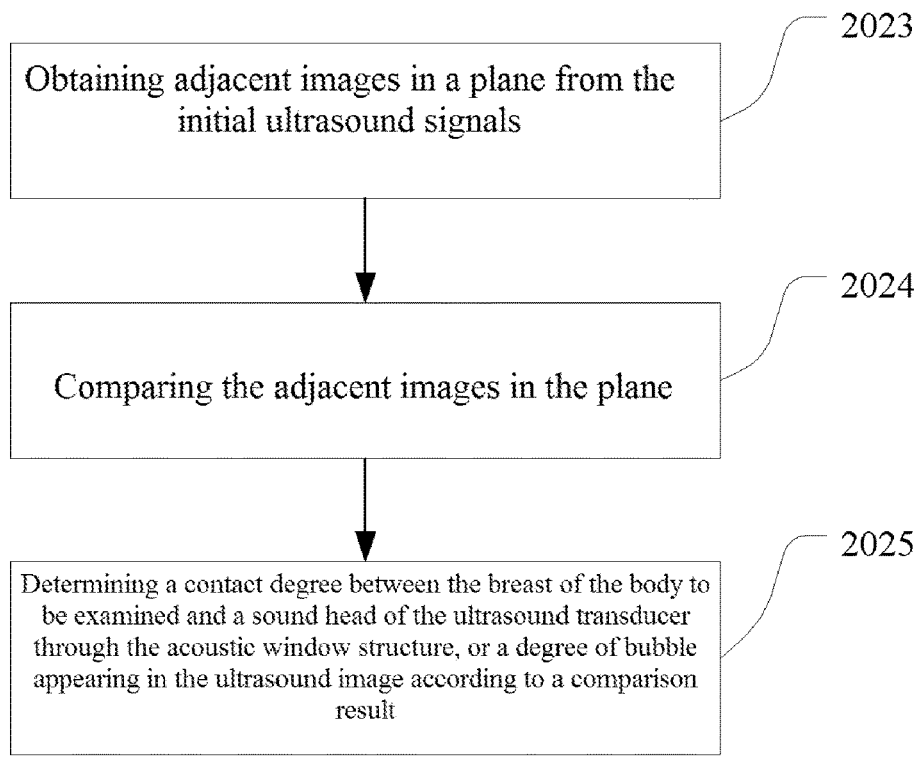
FIG. 19 is a schematic flow chart of a 3D imaging method according to a fourth embodiment of the present disclosure.

Referring to FIG. 19, it is a schematic flow chart of a 3D imaging method according to a fourth embodiment of the present disclosure, the fourth embodiment mainly describing a second method of echo analyzing by the echo analyzer.

The method includes:

Step 2023: obtaining adjacent images of the same plane from the initial ultrasound signal obtained by the ultrasound transducer;

Step 2024: comparing the adjacent images of the plane; and

Step 2025: determining a contact degree between the breast of the body to be examined and an acoustic head of the ultrasound transducer through the acoustic window, or a degree of bubble appearing in the ultrasound image according to the comparison result of Step 2024.

Figure 20:
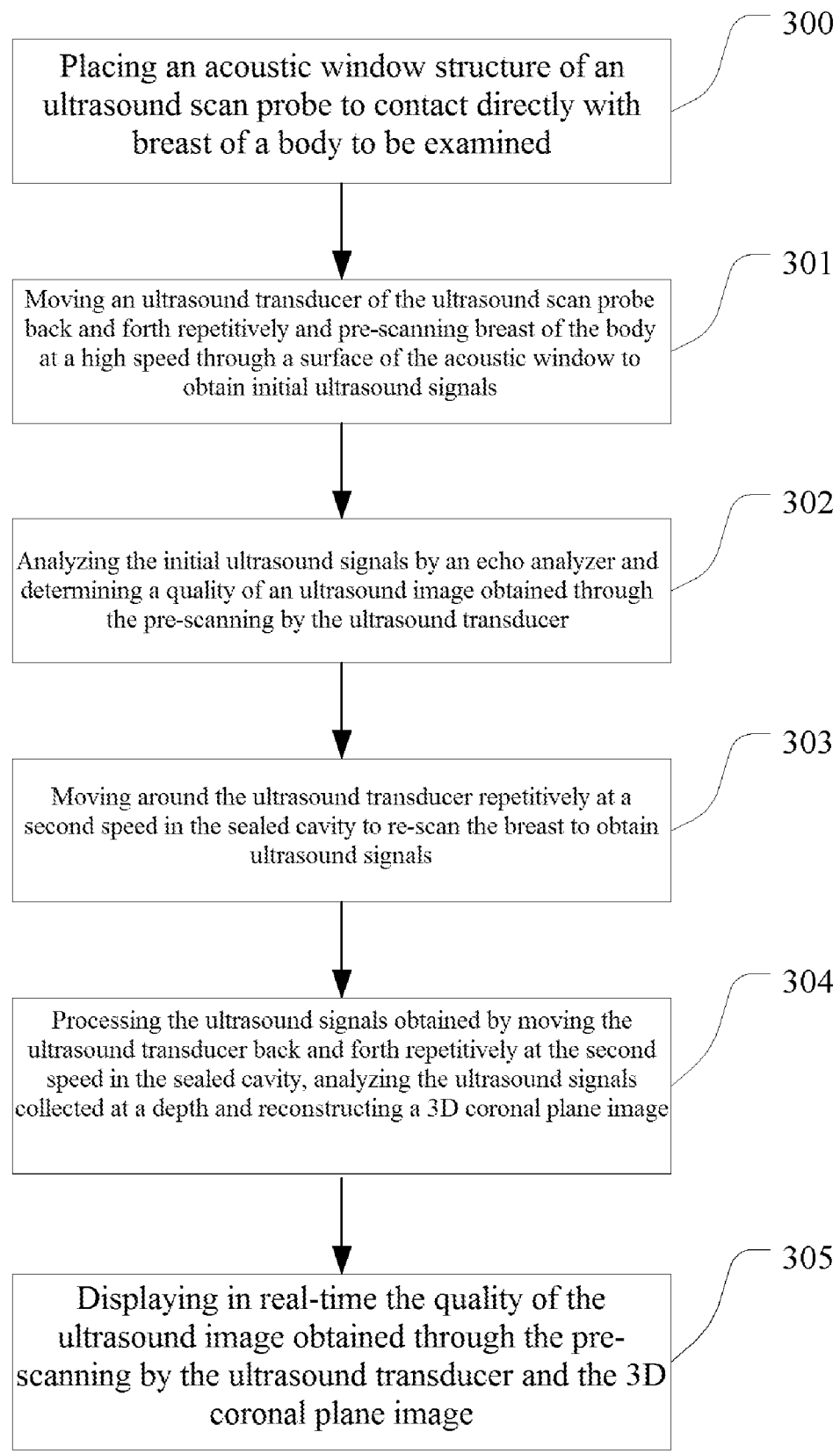
FIG. 20 is a schematic flow chart of a 3D imaging method according to a fifth embodiment of the present disclosure.

Referring to FIG. 20, it is a schematic flow chart of a 3D imaging method according to a fifth embodiment of the present disclosure, wherein the fifth embodiment specifically includes:

Step 300: placing an acoustic window of an ultrasound scan probe to contact directly with the breast of a body to be examined;

Step 301: moving an ultrasound transducer of the ultrasound scan probe repetitively back and forth at a first speed in the sealed chamber and pre-scanning the breast of the body at a high speed through a surface of the acoustic window to obtain an initial ultrasound signal;

Step 302: analyzing the initial ultrasound signal by an echo analyzer and determining a quality of an ultrasound image obtained through the pre-scanning by the ultrasound transducer;

Step 303: moving around the ultrasound transducer repetitively at a second speed in the sealed chamber to re-scan the breast to obtain ultrasound signals;

Step 304: processing the ultrasound signals obtained by moving around the ultrasound transducer repetitively at the second speed in the sealed chamber, analyzing the ultrasound signals collected at a depth and reconstructing a 3D coronal plane image; and Step 305: displaying in real-time the quality of the ultrasound image obtained through the pre-scanning by the ultrasound transducer and the 3D coronal plane image.

Where, the method further includes:

acquiring the position of the acoustic head in the sealed chamber when the ultrasound transducer is moving repetitively back and forth at the first speed or the second speed in the sealed chamber; the detailed embodiment of the acquiring process is similar to the process acquiring the position of the ultrasound transducer by employment of a sensor in the above-mentioned embodiment of a 3D ultrasound imaging device, therefore to repeat no more here; and indicating the current scanning position of the ultrasound transducer according to an indicating command; the detailed embodiment of the indicating process is similar to the aforementioned position indicating process by utilizing the position indicating unit, therefore to repeat no more here.

Figure 21:
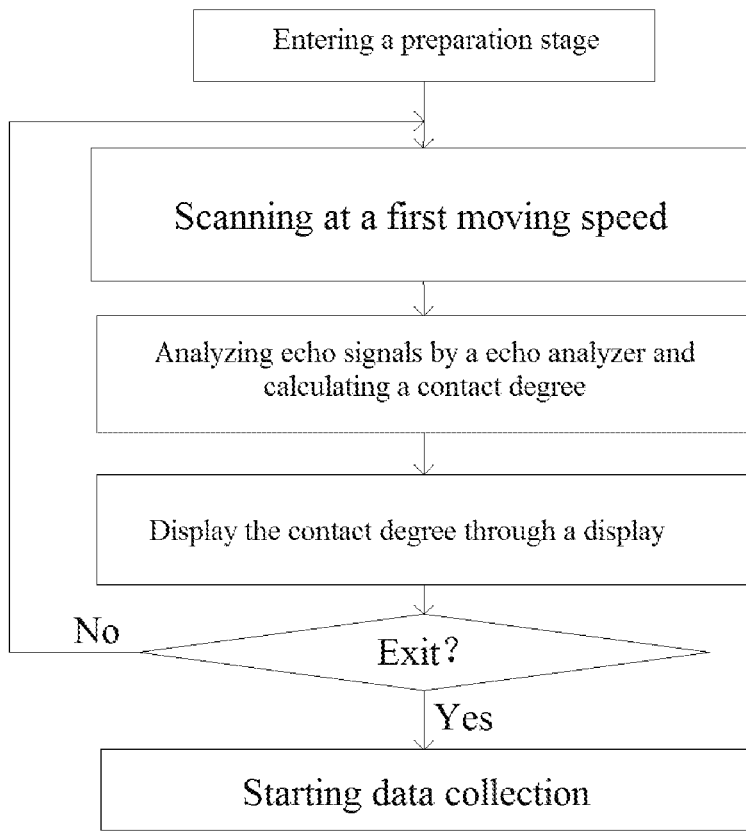
FIG. 21 is a schematic flow chart of an ultrasound scanning preparation stage using a 3D ultrasound imaging device according to an embodiment of the present disclosure.

Referring to FIG. 21, it is a schematic flow chart of an ultrasound scanning preparation stage using a 3D ultrasound imaging device according to an embodiment of the present disclosure: first, the 3D ultrasound imaging device enters a preparation stage and scans at a first moving speed, for example, finishes one round of scanning in 2 or 3 seconds. At this time, the echo analyzer inside the 3D ultrasound imaging device analyzes the collected echo signals, calculates the contact degree of the surface, and displays an indication on a corresponding display. The process is repeated until the user exits the loop.

Figure 22:
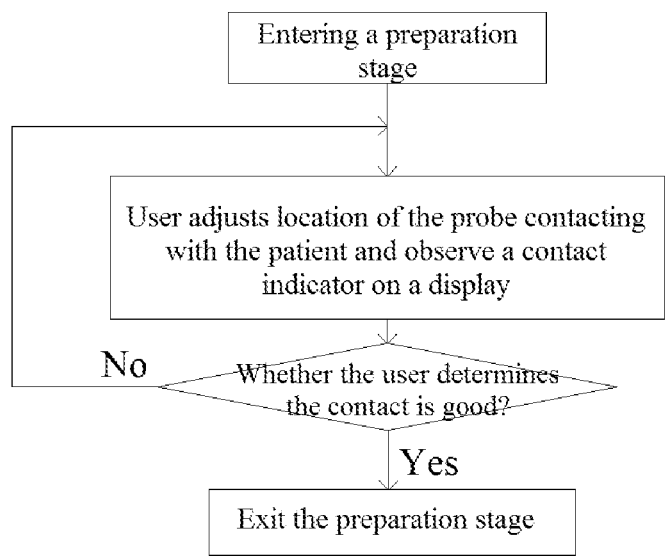
FIG. 22 is a schematic flow chart of an ultrasound scanning preparation stage using a 3D ultrasound imaging device according to another embodiment of the present disclosure.

Referring to FIG. 22, it is a schematic flow chart of an ultrasound scanning preparation stage using a 3D ultrasound imaging device according to another embodiment of the present disclosure. The condition of exiting the preparation stage may be the user's recognition of the current placement of the probe. The user observes the contact indication and adjusts the probe position, then decides whether to enter the data collection stage.

One or more advantages of implementing the embodiments of the present disclosure may include the following:

The 3D ultrasound imaging device and method employs an ultrasound probe acoustic with a window structure having relative high mechanical strength, and having good acoustic transparency, so it can keep good stability with the breast of the body to be examined.

In addition, the 3D ultrasound imaging device provided by the present disclosure uses an ultrasound probe to obtain ultrasound data quickly by way of pre-scanning, to evaluate the quality of the contacting or coupling between the ultrasonic window surface of the probe and the body tissue, and then performs regular formal scanning after adjustment if necessary. Therefore the success rate of breast scanning can be improved.

It should be understood for the ordinary and skilled person in the art that all or partial processes in the above-described exemplary methods can be realized by instructions of computer programs on the relevant hardware. These programs can be stored within computer-readable storage media. During their execution process, there may be some processes mentioned in the embodiments of those methods above. The storage medium can be a magnetic disk, compact disk, read only memory (ROM) or random access memory (RAM).

The foregoing embodiments with detailed descriptions represent several implementations of the present disclosure, but they should not be construed as limiting the scope of the present disclosure. It should be noted that, for those skilled in the art, a number of modifications and improvements can also be made without departing from the idea of the present disclosure, which is within the claimed scope of the present disclosure.

The invention claimed is:

1. An ultrasound imaging method using an ultrasound probe assembly including a housing, an acoustic window disposed at a bottom portion of the housing, and an ultrasound transducer disposed above the acoustic window and being movable across the acoustic window to scan a target object, at least a part of a lower surface of the acoustic window contacting with the target object, the ultrasound imaging method comprising:

pre-scanning the target object by moving the ultrasound transducer above the acoustic window at a first speed to obtain first ultrasound echo signals;

determining, based on the first ultrasound echo signals, a degree of contact between the acoustic window and the target object;

displaying an indication of the degree of contact between the acoustic window and the target object, wherein the indication comprises a two-dimensional graphical representation of an entire scanning plane of the acoustic window traversed by the ultrasound transducer, wherein the two-dimensional graphical representation is divided into at least one contact area and at least one noncontact area, wherein the at least one contact area corresponds to at least one region of the acoustic window having a higher degree of contact with the target object, and the at least one noncontact area corresponds to at least one region of the acoustic window having a lower degree of contact with the target object; and in response to a decision by a user to enter a data collection stage after observing the indication of the degree of contact:
re-scanning the target object by moving the ultrasound transducer above the acoustic window at a second speed to obtain second ultrasound echo signals, wherein the second speed is slower than the first speed;
acquiring an ultrasound image of the target object according to the second ultrasound echo signals; and
displaying the ultrasound image.

2. The ultrasound imaging method according to claim 1, wherein displaying an indication of the degree of contact comprises: generating a first ultrasound image according to the first ultrasound echo signals and displaying the first ultrasound image.

3. The ultrasound imaging method according to claim 1, wherein displaying an indication of the degree of contact between the acoustic window and the target object:
extracting a characteristic quantity from the first ultrasound echo signals; and
categorizing the first ultrasound echo signals according to the extracted characteristic quantity to obtain a category of the first ultrasound echo signals.

4. The ultrasound imaging method according to claim 3, wherein displaying an indication of the degree of contact between the acoustic window and the target object comprises:
generating a quality evaluation of the degree of contact according to the category of the first ultrasound echo signals; and
displaying the quality evaluation.

5. The ultrasound imaging method according to claim 1, wherein displaying an indication of the degree of contact between the acoustic window and the target object comprises:
comparing the first ultrasound echo signals with a pre-stored characteristic quantity.

6. The ultrasound imaging method according to claim 1, wherein pre-scanning comprises:
scanning the target object by using the ultrasound transducer at the first speed to obtain a first group of first ultrasound echo signals, and scanning the target object again by using the ultrasound transducer at the first speed to obtain a second group of first ultrasound echo signals.

7. The ultrasound imaging method according to claim 6, wherein displaying an indication of the degree of contact between the acoustic window and the target object comprises:
generating a first ultrasound image according to the second group of first ultrasound echo signals; and
displaying the first ultrasound image.

8. The ultrasound imaging method according to claim 6, wherein displaying an indication of the degree of contact between the acoustic window and the target object comprises:
extracting characteristic quantity from the second group of first ultrasound echo signals;
categorizing the second group of first ultrasound echo signals according to the extracted characteristic quantity to obtain a category of the second group of first ultrasound echo signals.

9. The ultrasound imaging method according to claim 8, wherein displaying an indication of the degree of contact between the acoustic window and the target object comprises:
generating a quality evaluation of the degree of contact according to the category of the second group of first ultrasound echo signals; and
displaying the quality evaluation.

10. The ultrasound imaging method according to claim 6, wherein displaying an indication of the degree of contact between the acoustic window and the target object comprises:
obtaining a first section image data in a pre-set plane from the first group of ultrasound echo signals;
obtaining a second section image data in the pre-set plane from the second group of ultrasound echo signals; and
comparing the first section image data with the second section image data.

11. The ultrasound imaging method according to claim 10, wherein displaying an indication of the degree of contact between the acoustic window and the target object comprises:
generating a quality evaluation of the degree of contact according to a comparison between the first section image data and the second section image data; and
displaying the quality evaluation.

12. The ultrasound imaging method according to claim 6, wherein the first area is an area where the acoustic window contacts with the target object and the second area is an area where the acoustic window contacts with air.

13. The ultrasound imaging method according to claim 1, further comprising: detecting a position of the ultrasound transducer relative to the acoustic window to acquire position information of the position of the ultrasound transducer relative to the acoustic window, and displaying the position information.

14. An ultrasound imaging device, comprising:
an ultrasound probe assembly comprising:
a housing;
an acoustic window disposed at a bottom portion of the housing and at least a part of a lower surface of the acoustic window contacts with a target object by an angle and a position;
an ultrasound transducer disposed above the acoustic window and configured to scan the target object;
an ultrasound transducer driving mechanism which is connected with the ultrasound transducer and drives the ultrasound transducer at a first speed to perform a first scanning to the target object to obtain first ultrasound echo signals;
a signal processor which:
receives and analyzes the first ultrasound echo signals,
determines, based on the first ultrasound echo signals, a degree of contact between the acoustic window and the target object, and
a display screen that displays an indication of the degree of contact between the acoustic window and the target object, wherein the indication comprises a two-dimensional graphical representation of an entire scanning plane of the acoustic window scanned by the ultrasound transducer, wherein the two-dimensional graphical representation is divided into at least one contact area and at least one noncontact area, wherein the at least one contact area corresponds to at least one two-dimensional region of the acoustic window having a higher degree of contact with the target object, and the at least one noncontact area corresponds to at least one two-dimensional region of the acoustic window having a lower degree of contact with the target object;

the ultrasound transducer driving mechanism further configured, in response to a decision by a user after observing the indication of the degree of contact on the display screen, re-scan the target object by moving the ultrasound transducer at a second speed to obtain second ultrasound echo signals, wherein the second speed is slower than the first speed the signal processor further configured to receive the second ultrasound echo signals and generate an ultrasound image based on the second ultrasound echo signals; and the display screen further configured to display the ultrasound image.

15. The ultrasound imaging device according to claim 14, wherein the signal processor comprises a first image processing unit which receives the first ultrasound echo signals and generates a first ultrasound image according to the first ultrasound echo signals, and the display screen further displays the first ultrasound image, to enable the user to determine the degree of contact between the acoustic window and the target object according to the first ultrasound image.

16. The ultrasound imaging device according to claim 14, wherein the signal processor further comprises an echo analyzer, wherein the echo analyzer comprises:
  a characteristic quantity extracting unit which extracts characteristic quantity from the first ultrasound echo signals;
  a categorizer which categorize the first ultrasound echo signals according to the characteristic quantity extracted by the characteristic quantity extracting unit to obtain a category of the first ultrasound echo signals; and
  a quality determining unit which determines the degree of contact between the acoustic window and the target object according to the category of the first ultrasound echo signals determined by the categorizer.

17. The ultrasound imaging device according to claim 16, wherein the quality determining unit further generates a quality evaluation of the degree of contact contact with the target object according to the category of the first ultrasound echo signals from the categorizer, and the display screen further displays the quality evaluation of the degree of contact between the acoustic window and the target object.

18. The ultrasound imaging device according to claim 14, wherein the ultrasound transducer is further configured to be driven at the first speed to scan the target object to obtain a first group of first ultrasound echo signals, and drives the ultrasound transducer at the first speed to re-scan the target object to obtain a second group of first ultrasound echo signals; and
  the signal processor determines the degree of contact between the acoustic window and the target object according to the first and/or second group of first ultrasound echo signals.

19. The ultrasound imaging device according to claim 18, wherein the signal processor comprises an echo analyzer, wherein the echo analyzer comprises:
  a section image acquiring unit which generates a first section image data of a predetermined section according to the first group of first ultrasound echo signals and generates a second section image data of the predetermined section according to the second group of first ultrasound echo signals;
  a comparator which compares the first section image data with the second section image data; and
  a quality determining unit which determines the degree of contact between the acoustic window and the target object according to a comparison result of the comparator.

20. The ultrasound imaging device according to claim 19, wherein the quality determining unit further generates a quality evaluation of the degree of contact between acoustic window and the target object according to the comparison result of the first section image data and the second section image data, and the display screen further displays the quality evaluation.

21. The ultrasound imaging device according to claim 14, wherein the display screen further comprises:
  a sub-display unit which is disposed on the housing and displays a first ultrasound image obtained by the first ultrasound echo signals and/or a second ultrasound image.

22. The ultrasound imaging device according to claim 14, further comprising:
  a position indicator which monitors a position of the ultrasound transducer relative to the acoustic window to acquire a position information of the position of the ultrasound transducer relative to the acoustic window.

23. The ultrasound imaging device according to claim 14, wherein a quality of the first scanning comprises: a contact degree between the acoustic window and the target object, a degree of bubble appearing in a first ultrasound image acquired by the first scanning and/or an image quality of the first ultrasound image acquired by the first scanning.

24. The ultrasound imaging method according to claim 1, wherein displaying an indication of the degree of contact between the acoustic window and the target object comprises:
  generating a first ultrasound image according to the first ultrasound echo signals; and determining a degree of bubble between the acoustic window and the target object according to the first ultrasound image; and
  determining the degree of contact between the acoustic window and the target object according to the first ultrasound echo signals according to the determined degree of bubble.

25. The ultrasound imaging method according to claim 1, wherein displaying an indication of the degree of contact between the acoustic window and the target object comprises:
  generating a first ultrasound image according to the first ultrasound echo signals; and
  determining an image quality of the first ultrasound image to present a contact degree between the acoustic window and the target object.

26. The ultrasound imaging method according to claim 1, wherein displaying an indication of the degree of contact between the acoustic window and the target object comprises:
  extracting a characteristic quantity from the first ultrasound echo signals;
  comparing the characteristic quantity from the first ultrasound echo signals with a pre-stored characteristic quantity;
  determining a category of the first ultrasound echo signals according to a result of the comparison between the characteristic quantity from the first ultrasound echo signals and the pre-stored characteristic quantity;
  determining the degree of contact between the acoustic window and the target object according to the category of the first ultrasound echo signals.

27. The ultrasound imaging method according to claim 2, further comprising:
   receiving a user indication of whether to adjust either or both of an angle of the acoustic window relative to the target object and a position of the acoustic window in a direction parallel to a contact interface in performing additional scanning of the target object at a second speed using the ultrasound transducer.

28. The ultrasound imaging method according to claim 1, wherein pre-scanning comprises performing moving the ultrasound transducer back and forth repetitively at the first speed in a sealed chamber;
   wherein re-scanning moving the ultrasound transducer back and forth repetitively at the second speed in the sealed chamber; and
   wherein a scanning track of the ultrasound probe assembly is fixed during each of the pre-scanning and the re-scanning.

29. The ultrasound imaging method according to claim 28, further comprising:
   processing ultrasound signals acquired by moving the ultrasound transducer back and forth repetitively at the second speed in the sealed chamber; and
   analyzing the ultrasound signals collected at a depth and reconstructing a 3D coronal plane image based on the analyzed ultrasound signals.

30. The ultrasound imaging method according to claim 1, wherein displaying the ultrasound image comprises:
   displaying the ultrasound image at a physical location corresponding to an actual scanning surface, with a display screen fixed to a top of the ultrasound probe assembly.

31. The ultrasound imaging method according to claim 10, wherein comparing the first section image data with the second section image data comprises:
   comparing texture characteristics of the first section image data with texture characteristics of the second section image data.

32. The ultrasound imaging method according to claim 1, further comprising:
   prior to re-scanning the target object at the second speed:
      pre-scanning the target object again by the ultrasound transducer at the first speed after the user has moved at least one of an angle or position of the acoustic window; and
      displaying a new indication of the degree of contact between the acoustic window and the target object.

33. The ultrasound imaging method according to claim 1, wherein the target object is pre-scanned by the ultrasound transducer at least twice at the first speed.

34. The ultrasound imaging method according to claim 1, wherein the indication of the degree of contact further includes a numerical value.

* * * * *